US006403764B1

(12) United States Patent
Dubaquie et al.

(10) Patent No.: US 6,403,764 B1
(45) Date of Patent: Jun. 11, 2002

(54) INSULIN-LIKE GROWTH FACTOR-1 PROTEIN VARIANTS

(75) Inventors: Yves Dubaquie, San Francisco; Paul J. Fielder, Redwood City; Henry B. Lowman, El Granada, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/477,924

(22) Filed: Jan. 5, 2000

Related U.S. Application Data

(60) Provisional application No. 60/170,261, filed on Dec. 9, 1999, and provisional application No. 60/115,010, filed on Jan. 6, 1999.

(51) Int. Cl.[7] ........................ A61K 38/00; A61K 38/28; C07K 2/00; C07K 14/00

(52) U.S. Cl. ............................ 530/300; 514/2; 514/12; 530/303; 530/350

(58) Field of Search ....................... 514/2, 12; 530/300, 530/303, 350, 324; 424/85.1, 184.1, 198.1

(56) References Cited

U.S. PATENT DOCUMENTS

| | | | | |
|---|---|---|---|---|
| 5,077,276 | A | 12/1991 | Ballard et al. | 514/2 |
| 5,106,832 | A | 4/1992 | Froesch et al. | 514/3 |
| 5,164,370 | A | 11/1992 | Ballard et al. | 514/12 |
| 5,273,961 | A | 12/1993 | Clark | 514/8 |
| 5,470,828 | A | 11/1995 | Ballard et al. | 514/12 |
| 5,514,646 | A | 5/1996 | Chance et al. | 514/3 |
| 5,565,428 | A | 10/1996 | Clark et al. | 514/12 |
| 5,714,460 | A | 2/1998 | Gluckman et al. | 514/3 |
| 5,741,776 | A | 4/1998 | Clark et al. | 514/12 |
| 5,750,373 | A | 5/1998 | Garrard et al. | 435/69.4 |
| 5,821,047 | A | 10/1998 | Garrard et al. | 435/5 |
| 5,834,250 | A | 11/1998 | Wells et al. | 435/7.1 |
| 5,891,722 | A | 4/1999 | Fuks et al. | 435/346 |
| 5,985,830 | A | 11/1999 | Acott et al. | 514/12 |
| 5,994,303 | A | 11/1999 | Arrhenius-Nyberg et al. | 514/12 |

FOREIGN PATENT DOCUMENTS

| | | |
|---|---|---|
| EP | 214826 | 3/1987 |
| EP | 742228 | 11/1996 |
| EP | 965596 | 12/1999 |
| WO | WO 89/05822 | 6/1989 |
| WO | WO 94/04569 | 3/1994 |
| WO | WO 96/33216 | 10/1996 |
| WO | WO 97/39032 | 10/1997 |
| WO | WO 98/45427 | 10/1998 |
| WO | WO 98/56406 | 12/1998 |
| WO | WO 99/32620 | 7/1999 |
| WO | WO 00/20023 | 4/2000 |
| WO | WO 00/23469 | 4/2000 |

OTHER PUBLICATIONS

Kristensen et al. Alanine Scanning Mutagenesis of Insulin. Journal of Biological Chemistry 272(20): 12978–12983, 1997.*

Nakagawa et al. Role of the phenylalanine B25 side chain in directing insulin interaction with its receptor. Steric and conformational effects. Journal of Biological Chemistry 261: 7332–7341, 1986.*

Bach and Rechler, "Insulin–like Growth Factor Binding Proteins" *Diabetes Reviews* 3:38–61 (1995).

Bagley et al., "A key functional role for the insulin–like growth factor 1 N–terminal pentapeptide" *Biochemical Journal* 259(3):665–671 (May 1, 1989).

Bar et al., "Tissue localization of perfused endothelial cell IGF binding protein is markedly altered by association with IGF–I" *Endocrinology* 127(6):3243–3245 (1990).

Baron et al., "Dexamethasone acts locally to inhibit longitudinal bone growth in rabbits" *American Journal of Physiology* 263(3 Pt 1):E489–E492 (Sep. 1992).

Barreca et al., "Short stature associated with high circulating insulin–like growth factor (IGF)–binding protein–1 and low circulating IGF–II: effect of growth hormone therapy" *Journal of Clinical Endocrinology & Metabolism* 83(10):3534–3541 (Oct. 1998).

Batch et al., "Abnormal regulation of insulin–like growth factor binding proteins in adolescents with insulin–dependent diabetes" *Journal of Clinical Endocrinology & Metabolism* 73(5):964–968 (Nov. 1991).

Baxter et al., "Recommendations for nomenclature of the insulin–like growth factor binding protein superfamily" *Endocrinology* 139(10):4036 (Oct. 1998).

Baxter et al., "Structural determinants for binary and ternary complex formation between insulin–like growth factor–I (IGF–I) and IGF binding protein–3" *Journal of Biological Chemistry* 267(1):60–65 (Jan. 5, 1992).

Bayne et al., "Structural analogs of human insulin–like growth factor I with reduced affinity for serum binding proteins and the type 2 insulin–like growth factor receptor" *Journal of Biological Chemistry* 263:6233–6239 (1988).

Bayne et al., "The C region of human isulin–like growth factor (IGF) I is required for high affinity binding to the type 1 IGF receptor" *Journal of Biological Chemistry* 264(19):11004–11008 (Jul. 5, 1988).

Bayne et al., "The roles of tyrosines 24, 31, and 60 in the high affinity binding of insulin–like growth factor–I to the type I insulin–like growth factor receptor" *Journal of Biological Chemistry* 265(26):15684–15652 (Sep. 15, 1990).

(List continued on next page.)

*Primary Examiner*—Elizabeth Kemmerer
*Assistant Examiner*—Bridget E. Bunner
(74) *Attorney, Agent, or Firm*—Janet E. Hasak

(57) ABSTRACT

IGF-I variants having an alanine, glycine, or serine amino acid residue at position 16,25,49 or at positions 3 and 49 of native-sequence IGF-I are provided that are useful to treat a disorder characterized by dysregulation of the GH/IGF axis in a mammal, such as a renal disorder.

3 Claims, 12 Drawing Sheets

OTHER PUBLICATIONS

Bereket et al., "Insulin treatment normalizes reduced free insulin–like growth factor–I concentrations in diabetic children" *Clinical Endocrinology* 45(3):321–326 (Sep. 1996).

Bereket et al., "Regulation of the insulin–like growth factor system by acute acidosis" *Endocrinology* 137(6):2238–2245 (Jun. 1996).

Blum et al., "Growth hormone resistance and inhibition of somatomedin activity by excess of insulin–like growth factor binding protein in uraemia" *Pediatric Nephrology* 5(4):539–544 (Jul. 1991).

Blum, W., "Insulin–like growth factors (IGFs) and IGF binding proteins in chronic renal failure: evidence for reduced secretion of IGFs" *Acta Paediatr. Scand.* 379 (Suppl):24–31 (1991).

Brems et al., "Altering the association properties of insulin by amino acid replacement" *Protein Engineering* 5(6):527–533 (1992).

Cascieri et al., "Mutants of human insulin–like growth factor I with reduced affinity for the type 1 insulin–like growth factor receptor" *Biochemistry* 27(9):3229–3233 (May 3, 1988).

Cascieri et al., "Structural analogs of human insulin–like growth factor (IGF) I with altered affinity for type 2 IGF receptors" *Journal of Biological Chemistry* 264:2199–2202 (1989).

Chernausek et al., "Proteolytic cleavage of insulin–like growth factor binding protein 4 (IGFBP–4) . Localization of cleavage site to non–homologous region of native IGFBP–4" *Journal of Biological Chemistry* 270(19):11377–11382 (May 12, 1995).

Clark and Robinson, "Up and down the growth hormone cascade" *Cytokine & Growth Factor Reviews* 7(1):65–80 (Jun. 1996).

Clemmons et al., "Competition for binding to insulin–like growth factor (IGF) binding protein–2, 3, 4, and 5 by the IGFs and IGF analogs" *Endocrinology* 131(2):890–895 (Aug. 1992).

Clemmons et al., "Discrete Alterations of the Insulin–like Growth Factor I Molecule Which Alter Its Affinity for Insulin–like Growth Factor–binding Proteins Result in Changes Bioactivity" *Journal of Biological Chemistry* 265(21):12210–12216 (1990).

Clemmons, D., "Insulin–like growth factor binding proteins and their role in controlling IGF actions" *Cytokine & Growth Factor Reviews* 8(1):45–62 (Mar. 1997).

Cohick and Clemmons, "The insulin–like growth factors" *Annu. Rev. Physiol.* 55:131–153 (1993).

Conover, C., "Insulin–like growth factor binding protein proteolysis in bone cell models" *Progress in Growth Factor Research* 6(2–4):301–309 (1995).

Cooke et al., "Solution Structure of Human Insulin–Like Growth Factor 1: A Nuclear Magnetic Resonance and Restrained Molecular Dynamics Study" *Biochemistry* 30:5484–5491 (1991).

Cox et al., "Recombinant human insulin–like growth factor (IGF)–binding protein–1 inhibits somatic growth stimulated by IGF–I and growth hormone in hypophysectomized rats" *Endocrinology* 135(5):1913–1920 (1994).

Crown and Holly, "The insulin–like growth factor system in critical illness: pathophysiology and therapeutic potential" *Clinical Nutrition* 14:321–328 (1995).

Cunningham and Wells, "Comparison of a structural and a functional epitope" *Journal of Molecular Biology* 234(3):554–563 (Dec. 5, 1993).

Cunningham et al., "High–Resolution Epitope Mapping of hGH–Receptor Interactions by Alanine–Scanning Mutagenesis" *Science* 244:1081–1085 (Jun. 1989).

Cunningham et al., "Production of an Atrial Natriuretic Peptide Variant that is Specific for Type A Receptor" *EMBO Journal* 13(11):2508–2515 (1994).

Davidson, M., "Effect of growth hormone on carbohydrate and lipid metabolism" *Endocrine Reviews* 8(2):115–131 (May 1987).

DeWolf et al., "Solution structure of a mini IGF–1" *Protein Science* 5(11):2193–2202 (Nov. 1996).

Dubaquie et al., "Total Alanine–Scanning Mutagenesis of Insulin–Like Growth Factor 1 (IGF–1) Identifies Differential Binding Epitopes for IGFBP–1 and IGFBP–3" *Biochemistry* 38(20):6386–6396 (1999).

Fuller et al., "Stimulation of Cardiac Protein Synthesis by Insulin–like Growth Factors" *Biochemical Society Transactions* 19:277S (1991).

Garrett et al., "Crystal structure of the first three domains of the type–1 insulin–like growth factor receptor" *Nature* 394(6691):395–399 (Jul. 23, 1998).

Guler et al., "Effects of recombinant insulin–like growth factor I on insulin secretion and renal function in normal human subjects" *Proc. Natl. Acad. Sci. USA* 86:2868–2872 (Apr. 1989).

Guler et al., "Insulin–like growth factor I increases glomerular filtration rate and renal plasma flow in man" *Acta Endocrinologica* 121:101–106 (1989).

Hall et al., "Serum levels of the low molecular weight form of insulin–like growth factor binding protein in healthy subjects and patients with growth hormone deficiency, acromegaly and anorexia nervosa" *Acta Endocrinologica* 118(3):321–326 (Jul. 1988).

Hammerman and Miller, "The growth hormone insulin–like factor axis in kidney revisited" *Am. J. Physiol.* 265:F1–F14 (1993).

Hammerman and Miller, "Therapeutic use of growth factors in renal failure" *J. Am. Soc. Nephrol.* 5:1–11 (1994).

Heding et al., "Biosensor measurement of the binding of insulin–like growth factors I and II and their analogues to the insulin–like growth factor–binding protein–3" *Journal of Biological Chemistry* 271(24):13948–13952 (Jun. 14, 1996).

Hirschberg et al., "Effects of insulin–like growth factor I on renal function in normal men" *Kidney International* 43:387–397 (1993).

Hise et al., "Influence of circulating insulin–like growth factor–I compared with that of intrarenal insulin–like growth factor–I on proximal nephron receptor density in rats" *Clinical Science* 83:233–239 (1992).

Hoogenberg et al., "Effect of growth hormone and insulin–like growth factor I on urinary albumin excretion: studies in acromegaly and growth hormone deficiency" *Acta Endocrinologica* 129:151–157 (1993).

Horber et al., "Differential effects of prednisone and growth hormone on fuel metabolism and insulin antagonism in humans" *Diabetes* 40(1):141–149 (Jan. 1991).

Hua et al., "Native and non–native structure in a protein–folding intermediate: spectroscopic studies of partially reduced IGF–I and an engineered alanine model" *Journal of Molecular Biology* 259(2):297–313 (Jun. 7, 1996).

Ikkos et al., "Glomerular filtration rate and renal plasma flow in acromegaly" *Acta Endocrinologica* 21:226–236 (1956).

Jansson et al., "Structural Changes in Insulin–Like Growth Factor (IGF) I Mutant Proteins Affecting Binding Kinetic Rates to IGF Binding Protein 1 and IGF–I Receptor" *Biochemistry* 36:4108–4117 (1997).

Jansson et al., "The Insulin–like Growth Factor (IGF) Binding Protein 1 Binding Epitope on IGF–I Probed by Heteronuclear NMR Spectroscopy and Mutational Analysis" *The Journal of Biological Chemistry* 273(38):24701–24707 (Sep. 18, 1998).

Joly et al., "Overexpressing of escherichia coli oxidoreductases increases recombinant insulin–like growth factor–I accumulation" *Proc. Natl. Acad. Sci. USA* 95:2773–2777 (Mar. 1998).

Jones et al., "Insulin–Like Growth Factors and Their Binding Proteins: Biological Actions" *Endocrine Reviews* 16(1):3–34 (1995).

Kalus et al., "Structure of the IGF–binding domain of the insulin–like growth factor–binding protein–5 (IGFBP–5): implications for IGF and IGF–I receptor interactions" *EMBO Journal* 17(22):6558–6572 (Nov. 16, 1998).

Kanety et al., "Long–term treatment of Laron type dwarfs with insulin–like growth factor–1 increases serum insulin––like growth factor–binding protein–3 in the absence of growth hormone activity" *Acta Endocrinologica* 128(2):144–149 (Feb. 1993).

Kupfer et al., "Enhancement of the anabolic effects of growth hormone and insulin–like growth factor I by use of both agents simultaneously" *J. Clin Invest.* 91:391–396 (1993).

Lee et al., "IGF binding proteins in growth–retarded children with chronic renal failure" *Pediatric Research* 26(4):308–315 (Oct. 1989).

Lee et al., "Insulin–Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF–I and IGF–II Receptors" *Mol. Endocrinol.* 2(5):404–411 (1988).

Lee et al., "Insulin–like growth factor binding protein–1: recent findings and new directions" *Proceedings of the Society for Experimental Biology & Medicine* 216(3):319–357 (Dec. 1997).

Lewitt et al., "Bioavailability of insulin–like growth factors (IGFs) in rats determined by the molecular distribution of human IGF–binding protein–3" *Endocrinology* 133:1797–1802 (1993).

Lewitt et al., "Insulin–like Growth Factor–binding Protein–1 Modulates Blood Glucose Levels" *Encocrinology* 129(4):2254–2256 (1991).

Liu et al., "Characterization of insulin–like growth factor–binding proteins in human serum from patients with chronic renal failure" *Journal of Clinical Endocrinology & Metabolism* 70(3):620–628 (Mar. 1990).

Loddick et al., "Displacement of insulin–like growth factors from their binding proteins as a potential treatment for stroke" *Proc. Natl. Acad. Sci. USA* 95(4):1894–1898 (Feb. 17, 1998).

Lowman and Wells, "Affinity maturation of human growth hormone by monovalent phage display" *Journal of Molecular Biology* 234(3):564–578 (Dec. 5, 1993).

Lowman et al., "Molecular mimics of insulin–like growth factor 1 (IGF–1) for inhibiting IGF–1: IGF–binding protein interactions" *Biochemistry* 37(25):8870–8878 (Jun. 23, 1998).

Lowman, H., "Phage display of peptide libraries on protein scaffolds" *Methods in Molecular Biology*, Chapter 24, 87:249–264 (1998).

Manes et al., "Functional eptiope mapping of insulin–like growth factor I (IGF–I) by Anti–IGF–I monoclonal antibodies" *Endocrinology* 138(3):905–915 (1997).

Martin and Baxter, "Regulation and actions of the insulin–like growth factor binding proteins" *Current Opinion in Endocrinology and Diabetes* pp. 16–21 (1994).

McCarthy et al., "Cortisol inhibits the synthesis of insulin–like growth factor–I in skeletal cells" *Endocrinology* 126(3):1569–1575 (Mar. 1990).

McInnes and Sykes, "Growth factor receptors: structure, mechanism, and drug discovery" *Biopolymers* 43(5):339–366 (1997).

Miller et al., "Effects of IGF–I on renal function in end–stage chronic renal failure" *Kidney International* 46:201–207 (1994).

Moses, A., "Recombinant insulinlike growth factor–I as therapy in states of altered carbohydrate homeostasis" *Current Opinion in Endocrinology and Diabetes* 4:16–25 (1997).

Murphy et al., "Phenotypic manifestations of insulin–like growth factor binding protein–1 (IGFBP–1) and IGFBP–3 overexpression in transgenic mice" *Progress in Growth Factor Research* 6(2–4):425–432 (s 1995).

O'Shea and Layish, "Growth hormone and the kidney: a case presentation and review of the literature" *J. Am. Soc. Nephrol.* 3:157–161 (1992).

O'Shea et al., "Effects of IGF–I on renal function in patients with chronic renal failure" *Am. J. Physiol.* 264:F917–F922 (1993).

Oh et al., "Characterization of the affinities of insulin–like growth factor (IGF)–binding proteins 1–4 for IGF–I, IGF–II, IGF–I/insulin hybrid, and IGF–I analogs" *Endocrinology* 132:1337–1344 (1993).

Peterkofsky et al., "Elevated Activity of Low Molecular Weight Insulin–Like Growth Factor–Binding Proteins in Sera of Vitamin C–Deficient and Fasted Guinea Pigs" *Endocrinology* 128(4):1769–1779 (1991).

Powell et al., "Characterization of insulin–like growth factor binding protein–3 in chronic renal failure serum" *Pediatric Research* 33(2):136–143 (Feb. 1993).

Powell et al., "Modulation of growth factors by growth hormone in children with chronic renal failure." *Kidney International* 51(6):1970–1979 (Jun. 1997).

Powell et al., "Serum concentrations of insulin–like growth factor (IGF)–1, IGF–2 and unsaturated somatomedin carrier proteins in children with chronic renal failure" *American Journal of Kidney Diseases* 10(4):287–292 (Oct. 1987).

Quigley and Baum, "Effects of growth hormone and insulin––like growth factor I on rabbit proximal convoluted tubule transport" *J. Clin. Invest.* 88:368–374 (1991).

Rajkumar et al., "Growth retardation and hyperglycemia in insulin–like growth factor binding protein–1 transgenic mice" *Endocrinology* 136(9):4029–4034 (Sep. 1995).

Rosenfeld et al., "IGF–1 treatment of syndromes of growth hormone insensitivity" *The insulin–like growth factors and their regulatory proteins*, Baxter et al. eds., Amsterdam:Excerpta Medica pp. 457–463 (1994).

Ross et al., "Critically ill patients have high basal growth hormone levels with attenuated oscillatory activity associated with low levels of insulin–like growth factor–I" *Clinical Endocrinology* 35(1):47–54 (Jul. 1991).

Sapir et al., "The role of alanine and glutamine in steroid–induced nitrogen wasting in man" *Clinical Science & Molecular Medicine* 53(3):215–220 (Sep. 1977).

Scharf et al., "Insulin–like growth factor–I serum concentrations and patterns of insulin–like growth factor binding proteins in patients with chronic liver disease" *Journal of Hepatology* 25(5):689–699 (Nov. 1996).

Shmueli et al., "High insulin–like growth factor binding protein 1 levels in cirrhosis: link with insulin resistance" *Hepatology* 24(1):127–133 (Jul. 1996).

Simmons et al., "Increased proteolysis. An effect of increases in plasma cortisol within the physiologic range" *Journal of Clinical Investigation* 73(2):412–420 (Feb. 1984).

Simpson et al., "Insulin–like growth factor–I and diabetes. A review" *Growth Hormone and IGF Research* 8:83–95 (1998).

Slieker et al., "Insulin and IGF–I Analogs: Novel Aproaches to Improved Insulin Pharmacokinetics" *Adv. Experimental Med. Biol.* 343:25–32 (1994).

Terasawa et al., "Solution structure of human insulin–like growth factor II; recognition sites for receptors and binding proteins" *EMBO Journal* 13(23):5590–5597 (Dec. 1, 1994).

Thrailkill et al., "Dual hormonal replacement therapy with insulin and recombinant human insulin–like growth factor (IGF)–I in insulin–dependent diabetes mellitus: effects on the growth hormone/IGF/IGF–binding protein system" *Journal of Clin. Endocrinol. & Metab.* 82(4):1181–1187 (Apr. 1997).

Tomas et al., "Insulin–like growth factor–I (IGF–I) and especially IGF–I variants are anabolic in dexamethasone–treated rats" *Biochemical Journal* 282(Pt 1):91–97 (Feb. 15, 1992).

Tonshoff et al., "Decreased hepatic insulin–like growth factor (IGF)–I and increased IGF binding protein–1 and –2 gene expression in experimental uremia" *Endocrinology* 138(3):938–946 (Mar. 1997).

Tonshoff et al., "Insulin–like growth factors (IGF) and IGF binding proteins in children with chronic renal failure" *Progress in Growth Factor Research* 6(2–4):481–491 (1995).

Tonshoff et al., "Serum insulin–like growth factors (IGFs) and IGF binding proteins 1, 2, and 3 in children with chronic renal failure: relationship to height and glomerular filtration rate" *Journal of Clinical Endocrinology & Metabolism* 80(9):2684–2691 (Sep. 1995).

Tonshoff et al., "Serum insulin–like growth factors and their binding proteins in children with end–stage renal disease" *Pediatric Nephrology* 10(3):269–274 (Jun. 1996).

Torres et al., "Solution structure of human insulin–like growth factor II. Relationship to receptor and binding protein interactions" *Journal of Molecular Biology* 248(2):385–401 (Apr. 28, 1995).

Trainer et al., "Pyridostigmine partially reverses dexamethasone–induced inhibition of the growth hormone response to growth hormone–releasing hormone" *Journal of Endocrinology* 134(3):513–517 (Sep. 1992).

Ullrich et al., "Insulin–like growth factor I receptor primary structure: comparison with insulin receptor suggests structural determinants that define functional specificity" *EMBO Journal* 5(10):2503–2512 (1986).

Umpleby et al., "Effects of Insulin–like Growth Factor–I (IGF–I), Insulin and Combined IGF–I–insulin Infusions on Protein Metabolism in Dogs"0 *Eur. J. Clin. Invest.* 24:337–344 (1994).

Underwood et al., "IGFs: Function and Clinical Importance 6 Therapy With Recombinant Human Insulin–like Growth Factor I in Children With Insensitivity to Growth Hormone and in catabolic conditions" *J. Internal Med.* 234:571–577 (1993).

Walker et al., "Stimulation of statural growth by recombinant insulin–like growth factor I in a child with growth hormone insensitivity syndrome (Laron type)" *J. Pediatr.* 121:641–646 (1992).

Wells, J. A., "Additivity of Mutational Effects in Proteins" *Biochemistry* 29(37):8509–8517 (Sep. 18, 1990).

Woolfson et al., "Insulin to inhibit protein catabolism after injury" *New England J. of Medicine* 300 (1):14–17 (Jan. 4, 1979).

Bogan and Thorn, "Anatomy of hot spots in protein interfaces" *Journal of Molecular Biology* 280(1):1–9 (Jul. 3, 1998).

Conover, "Potentiation of insulin–like growth factor (IGF) action by IGF–binding protein–3: studies of underlying mechanism" *Endocrinology* 130(6):3191–3199 (Apr. 1992).

King et al., "Production and characterization of recombinant insulin–like growth factor–I (IGF–I) and potent analogues of IGF–I, with Gly or Arg substituted for $Glu^3$, following their expression in *Escherichia coli* as fusion proteins" *Journal of Molecular Endocrinology* 8(1):29–41 (Feb. 1992).

Magee et al., "Insulin–like growth factor I and its binding proteins: a study of the binding interface using B–domain analogues" *Biochemistry* 38(48):15863–15870 (Nov. 30, 1999).

* cited by examiner

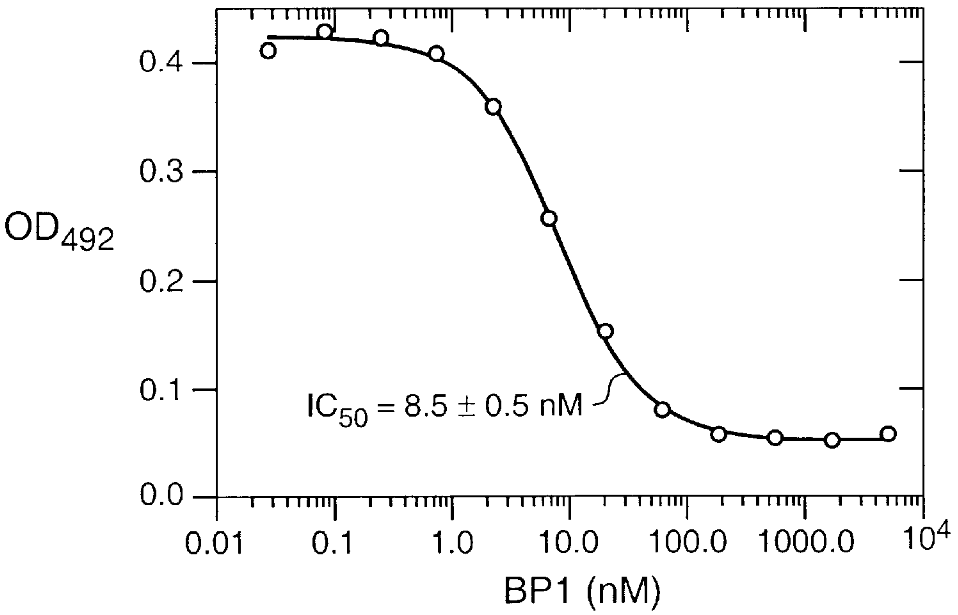
FIG._1A
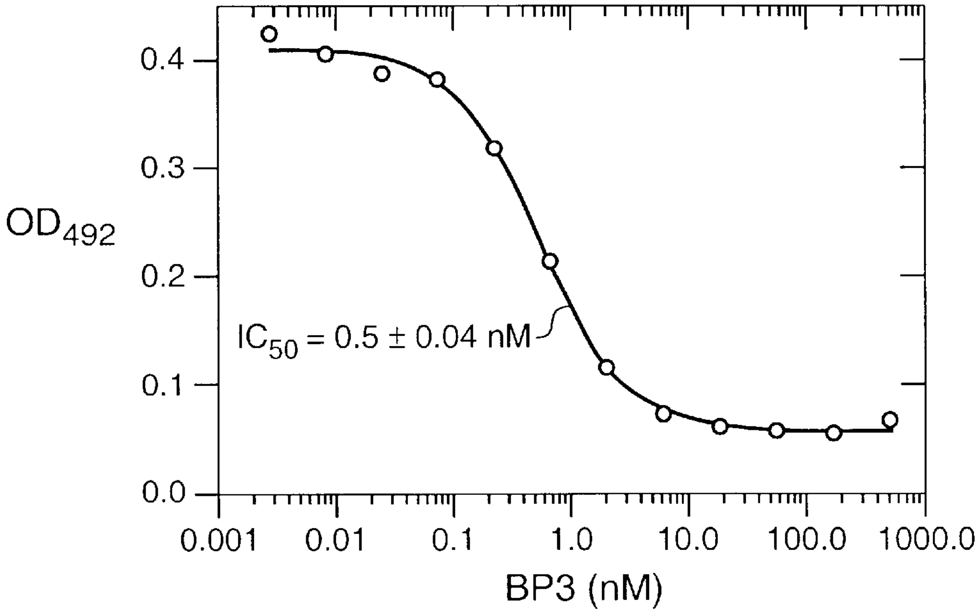
FIG._1B

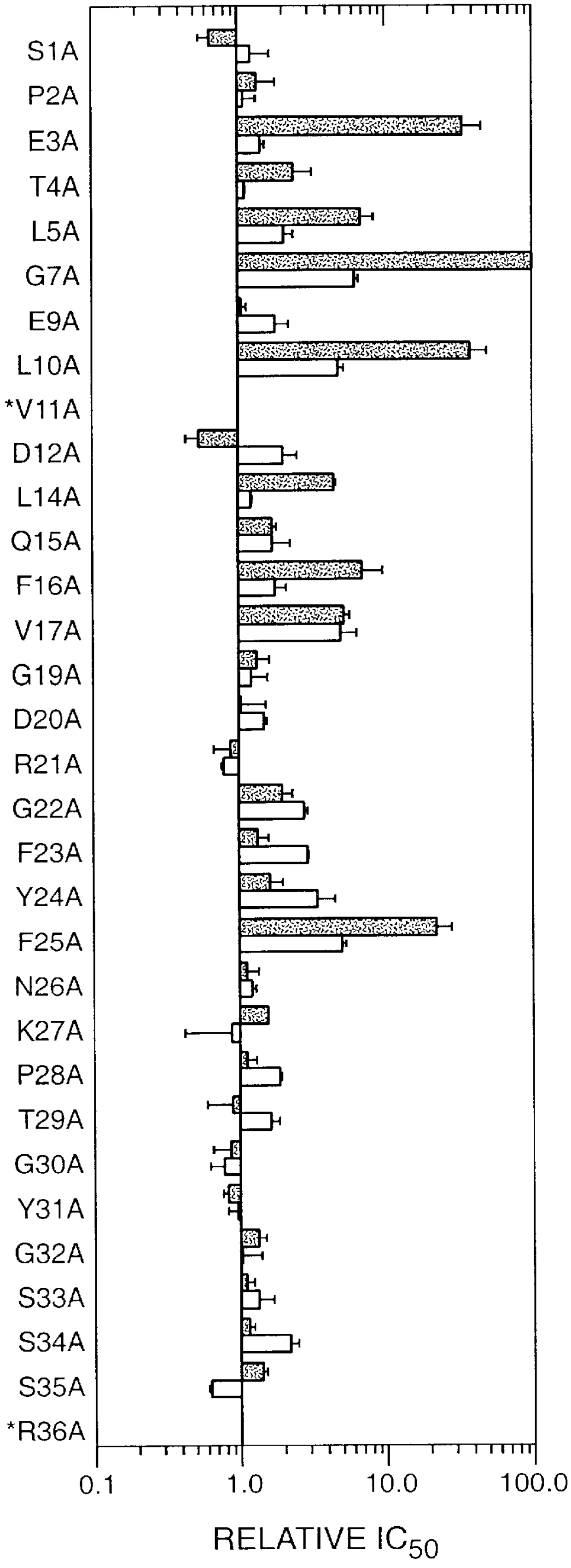
FIG._2A

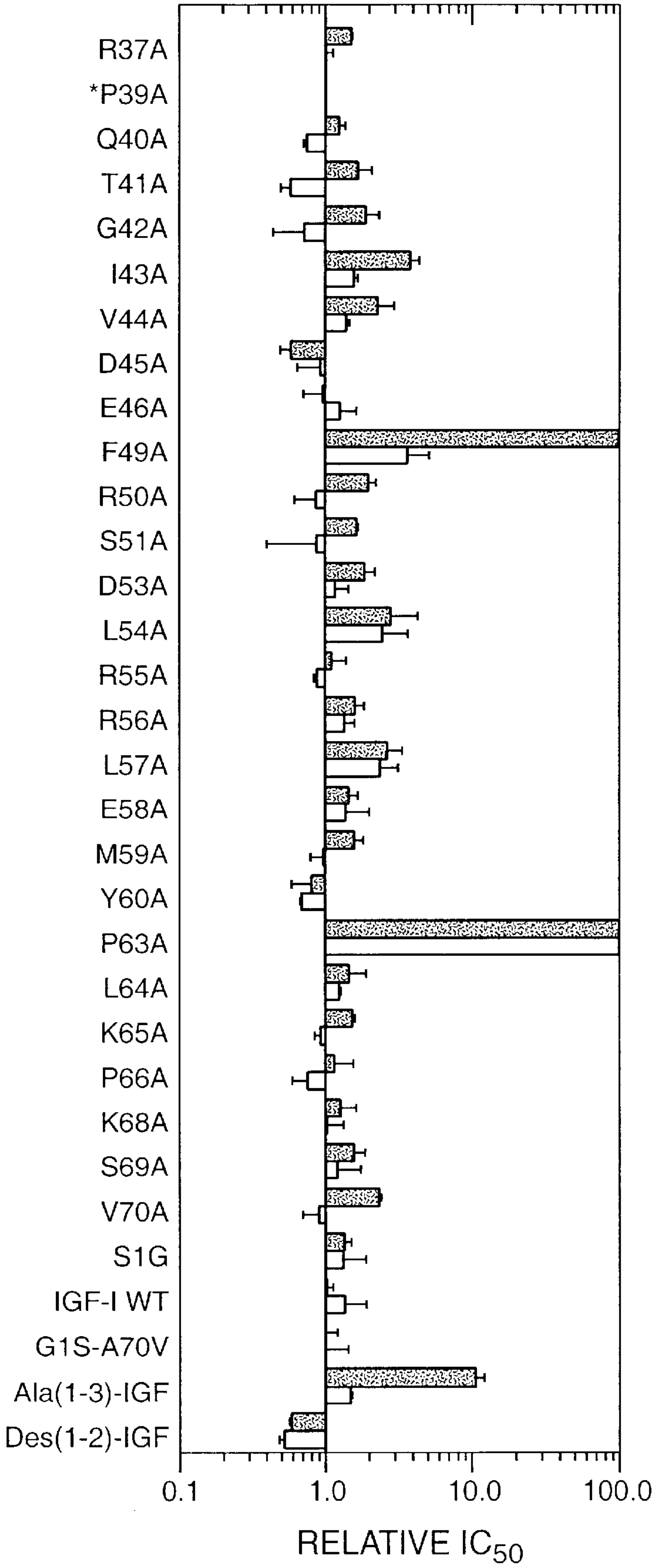
FIG._2B

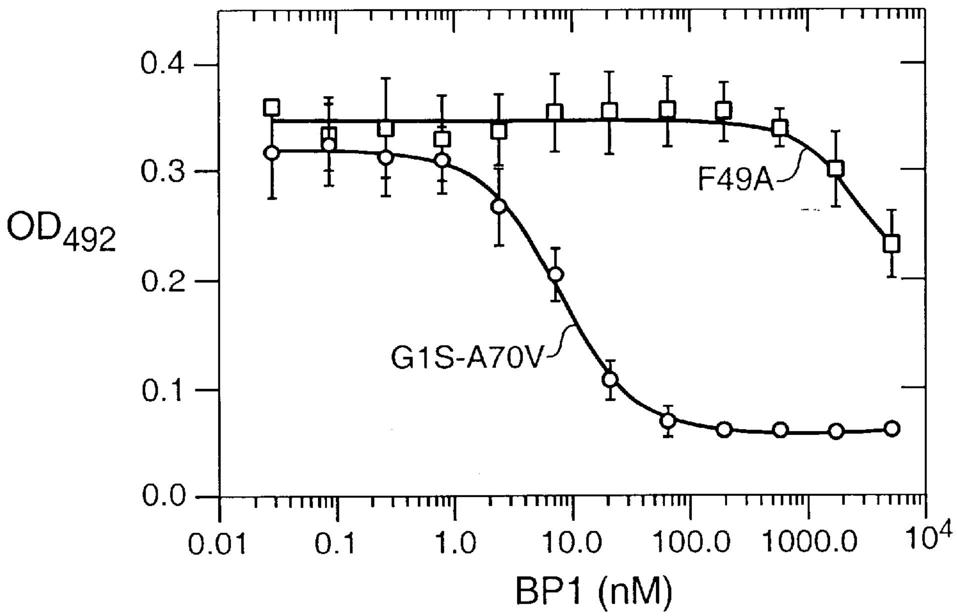
FIG._3A
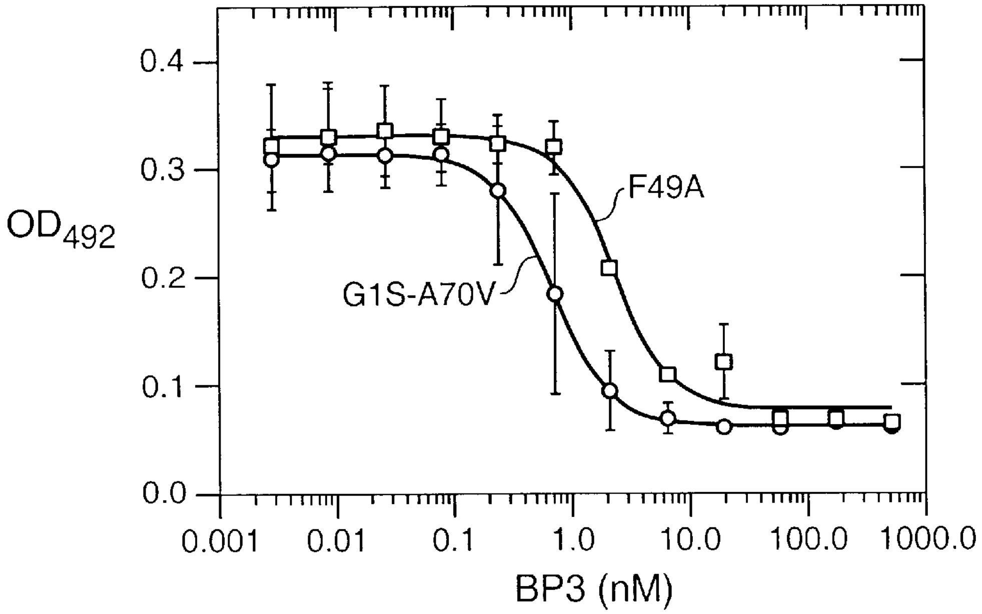
FIG._3B

```
                  10        20                         30
wtIGF     GPETLCGAELVDALQFVCGDRGFYFNKPT----------------GYGS
             .***..**.** .***.***..   *                * *.
proin-   FVNQHLCGSHLVEALYLVCGERGFFYTPKTRREAEDLQVGQVELGGGPGA
sulin            10        20        30        40        50
             .***..**.** .***.***..   *
insulin  FVNQHLCGSHLVEALYLVCGERGFFYTPKT
(B chain)        10        20        30


                     40        50        60        70
wtIGF    SSRRA-------PQTGIVDECCFRSCDLRRLEMYCAPLKPAKSA
         .* ..        . ***..**   * * .** **
proin-   GSLQPLALEGSLQKRGIVEQCCTSICSLYQLENYCN
sulin            60        70        80
                        ***..**   * * .** **
insulin                  GIVEQCCTSICSLYQLENYCN
(A chain)               31       40        50
```

FIG._4

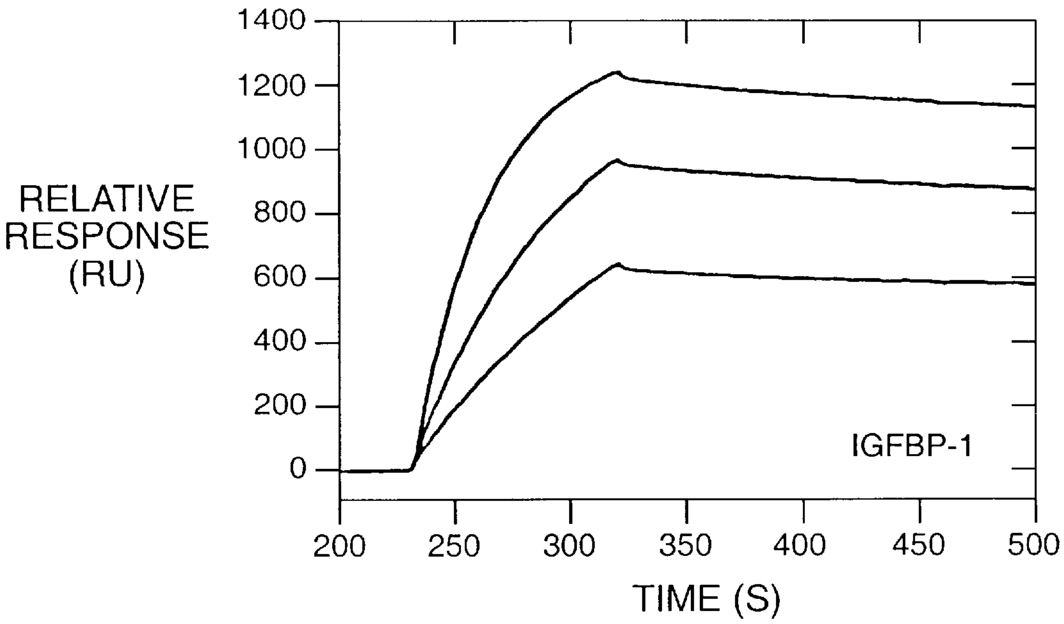
FIG._5A
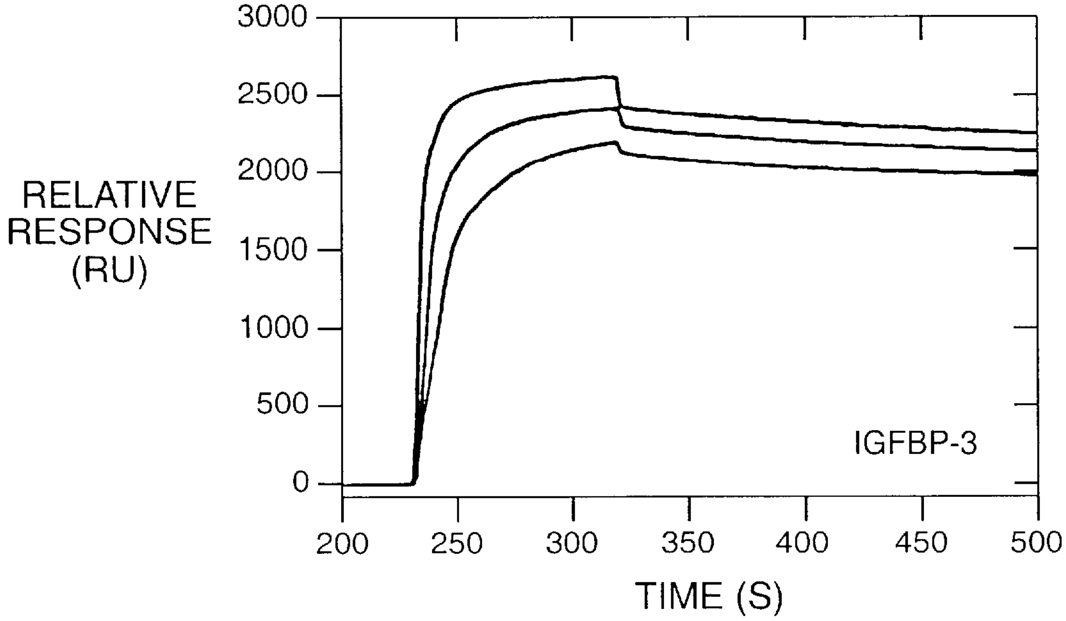
FIG._5B

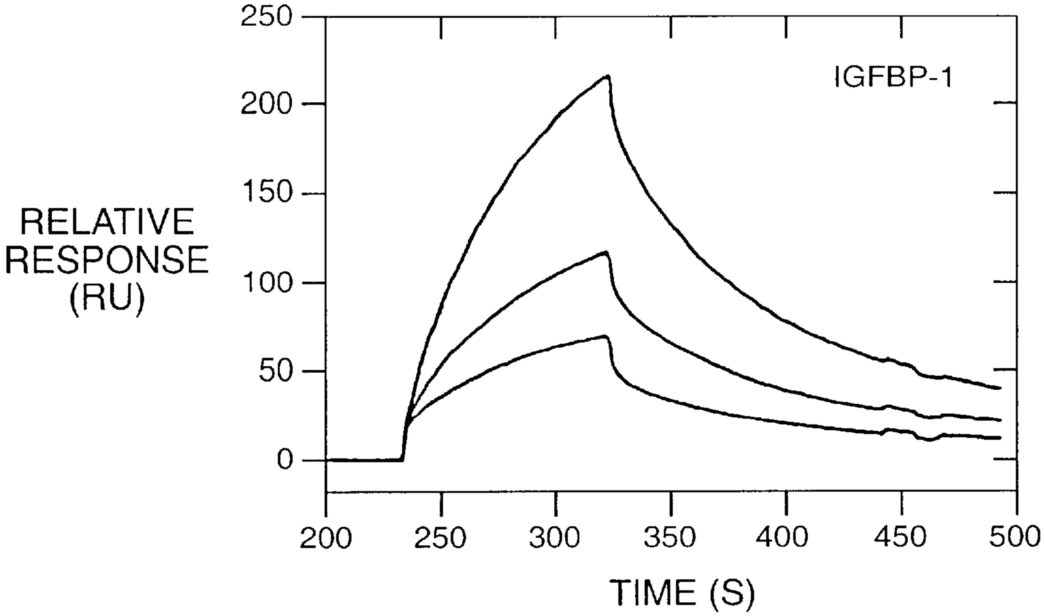
FIG._5C
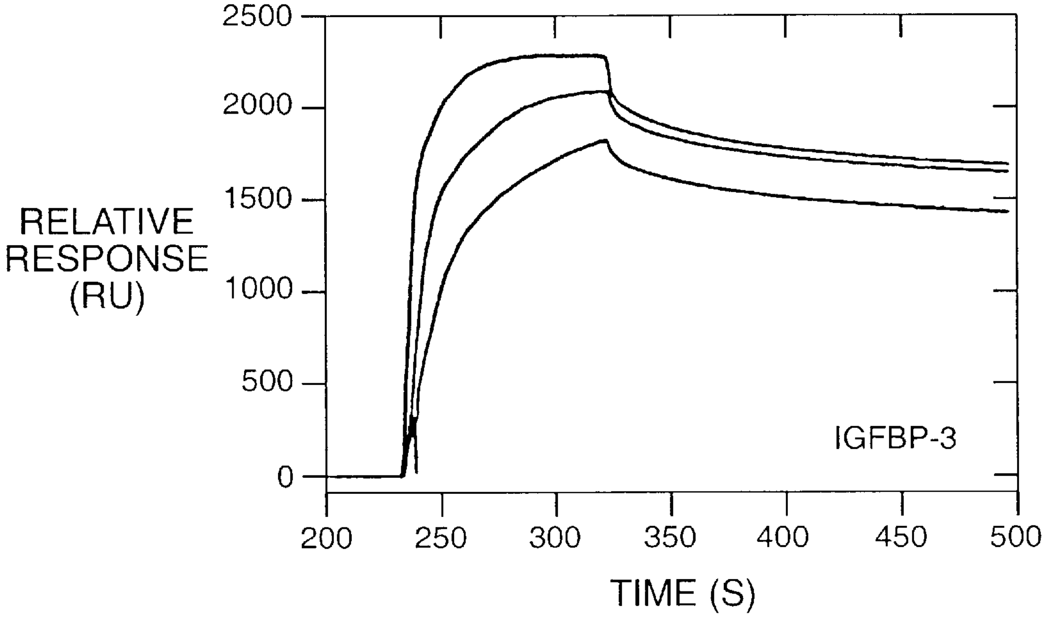
FIG._5D

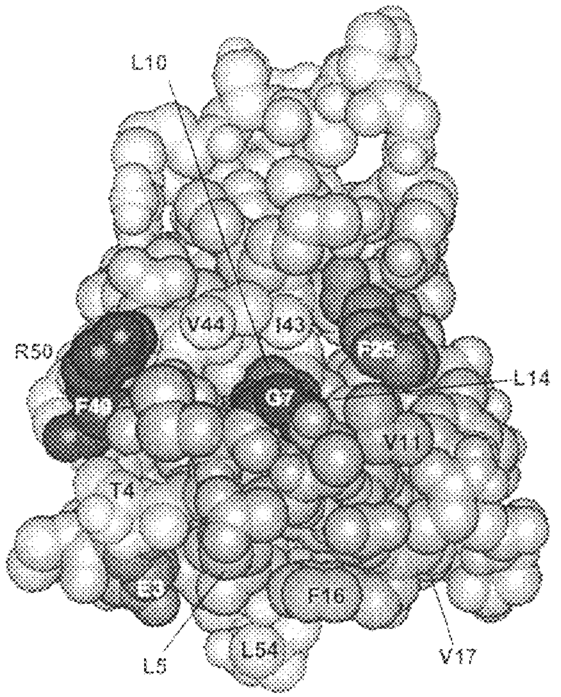
FIG._6A
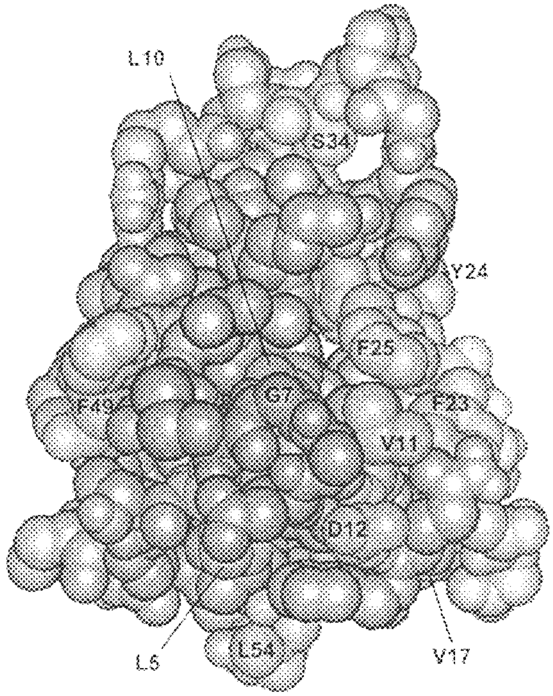
FIG._6B

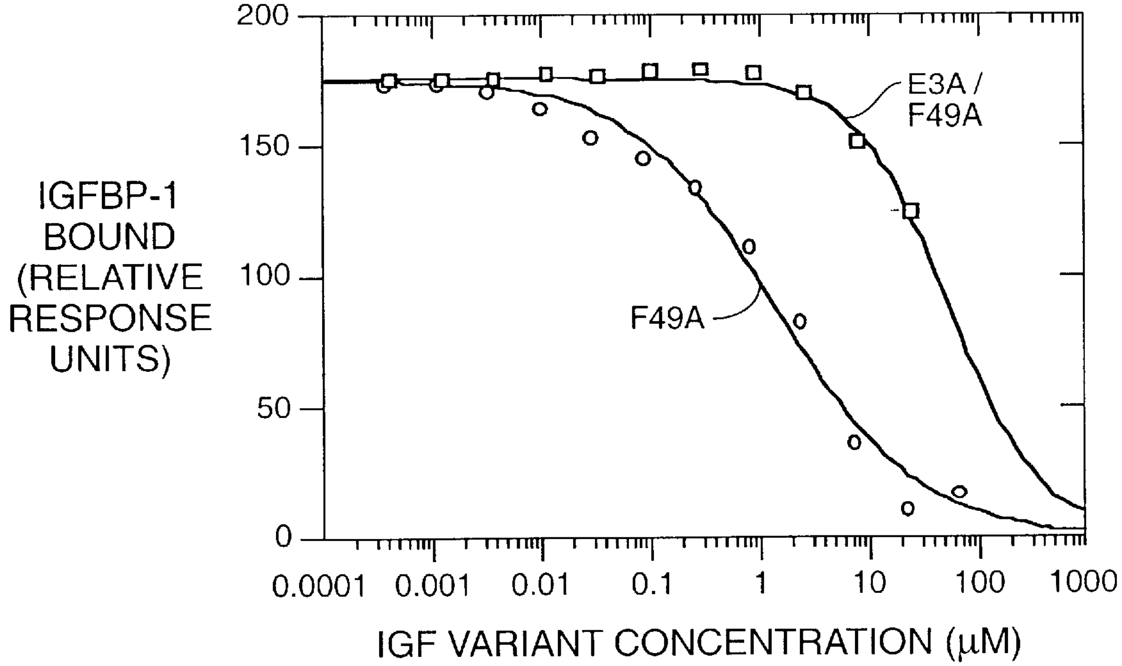
*FIG._7*
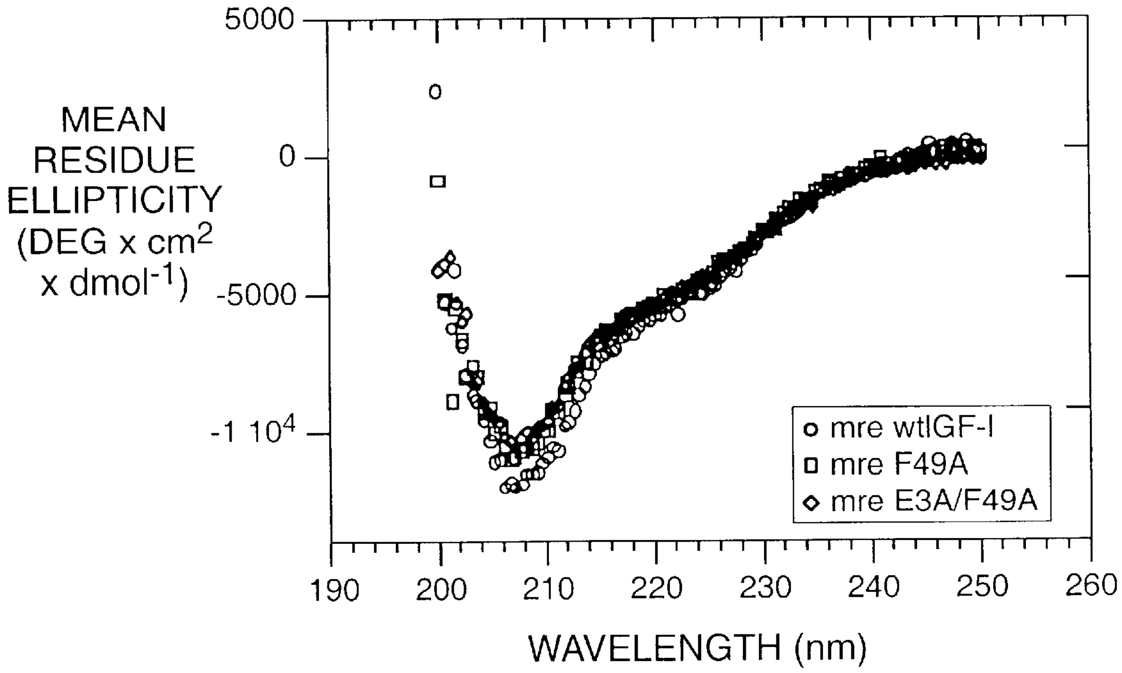
*FIG._11*

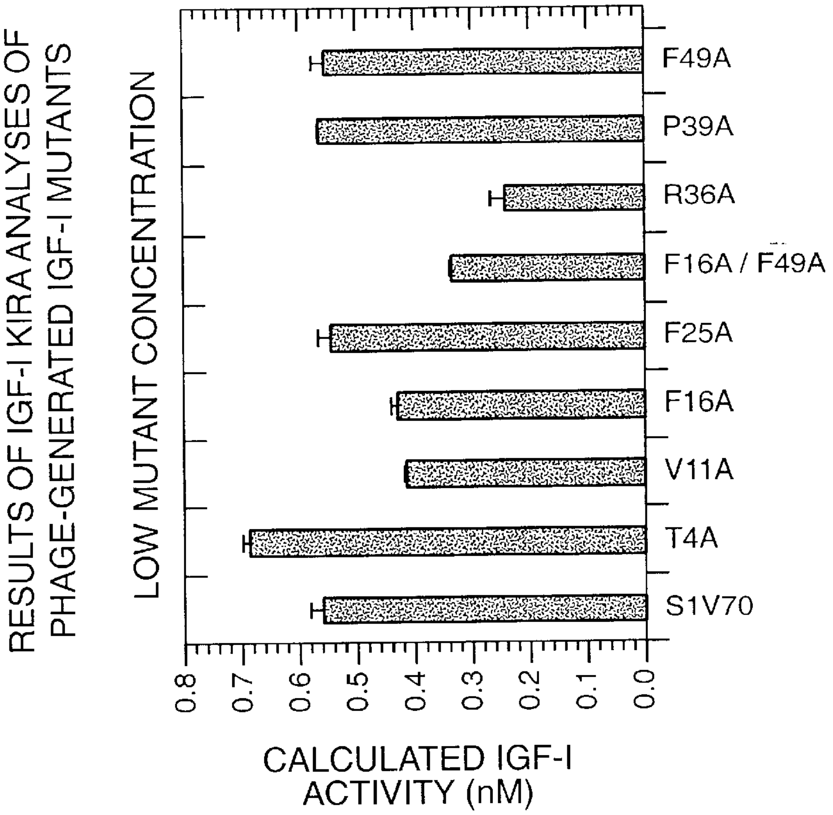
FIG._8B
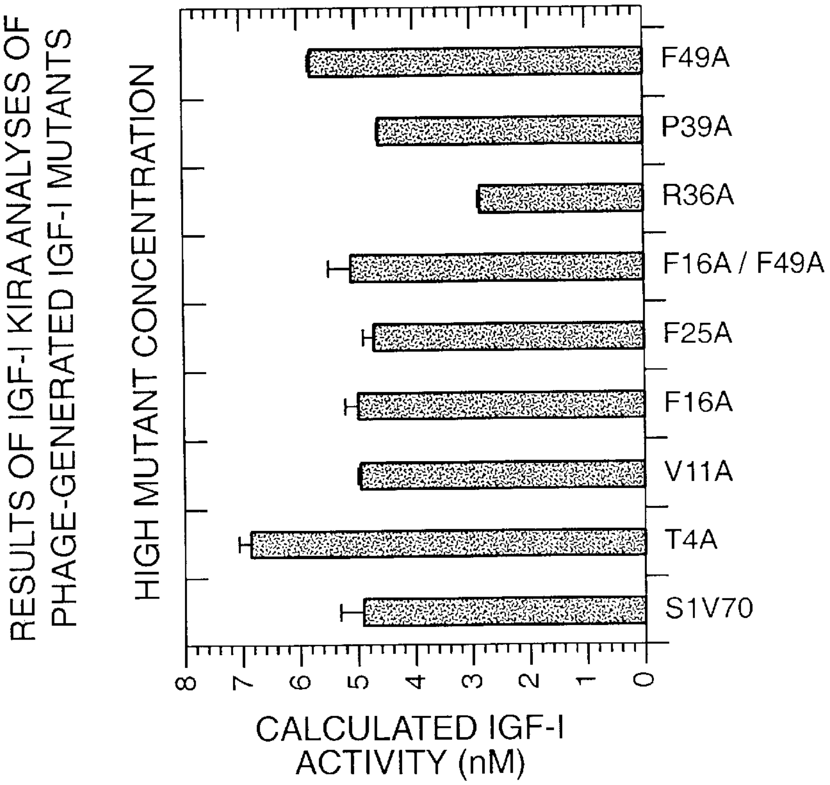
FIG._8A

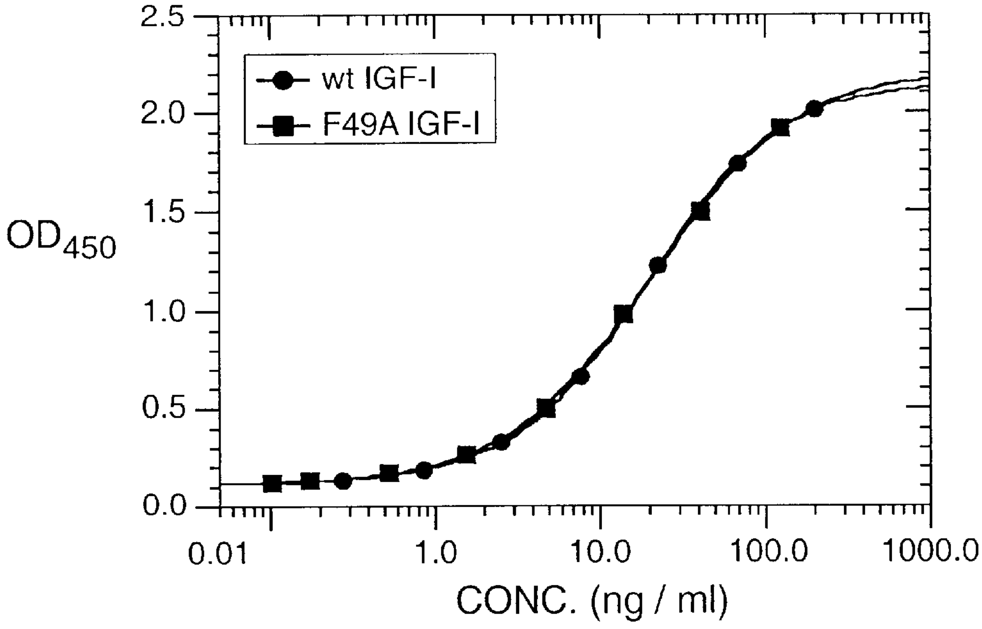
FIG._9A
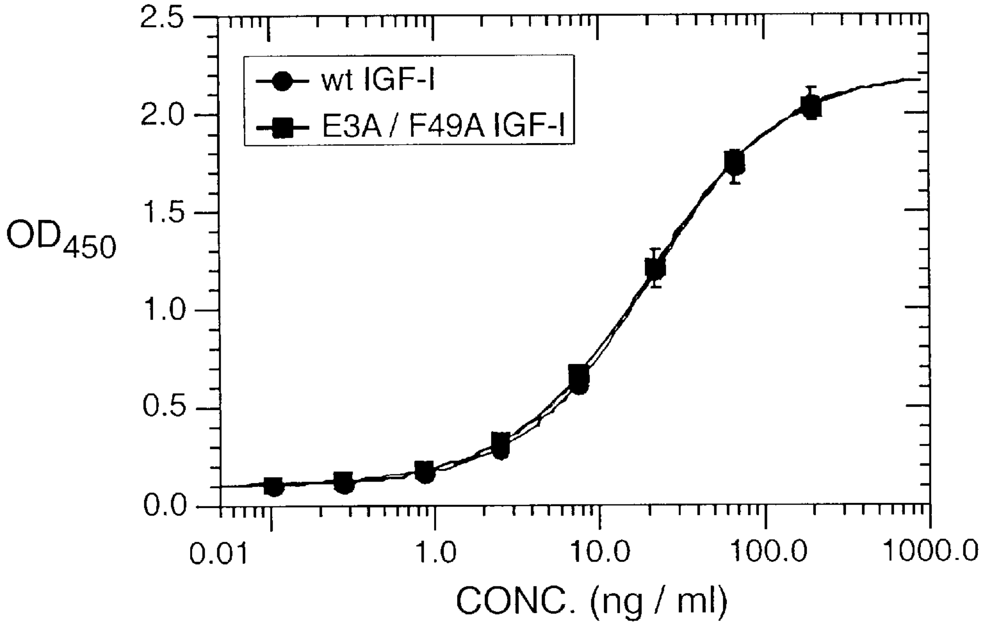
FIG._9B

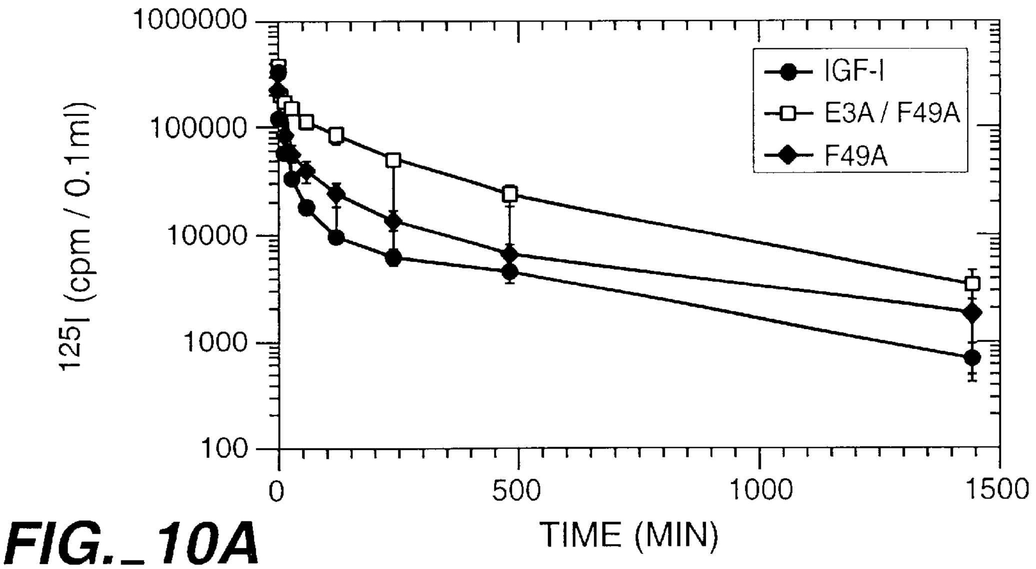
FIG._10A
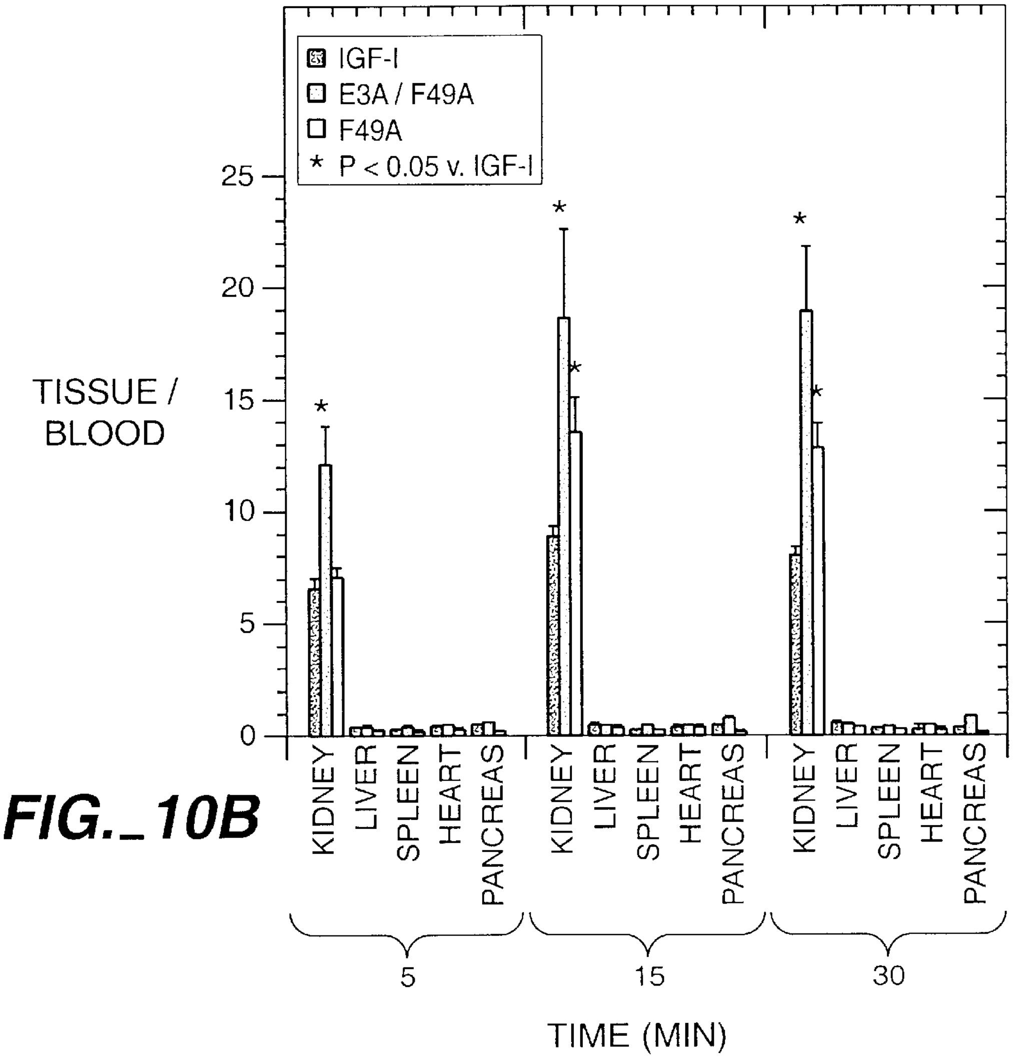
FIG._10B

SEQUENCE LISTING

```
<160> NUMBER OF SEQ ID NOS: 6

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu V al Asp Ala Leu Gln
  1               5                  10                  15

Phe Val Cys Gly Asp Arg Gly Phe Tyr Phe A sn Lys Pro Thr Gly
             20                  25                  30

Tyr Gly Ser Ser Ser Arg Arg Ala Pro Gln T hr Gly Ile Val Asp
             35                  40                  45

Glu Cys Cys Phe Arg Ser Cys Asp Leu Arg A rg Leu Glu Met Tyr
             50                  55                  60

Cys Ala Pro Leu Lys Pro Ala Lys Ser Ala
             65                  70


<210> SEQ ID NO 2
<211> LENGTH: 86
<212> TYPE: PRT
```

-continued

<213> ORGANISM: Homo sapiens

<400> SEQUENCE: 2

```
Phe Val Asn Gln His Leu Cys Gly Ser His L eu Val Glu Ala Leu
  1               5                  10                  15

Tyr Leu Val Cys Gly Glu Arg Gly Phe Phe T yr Thr Pro Lys Thr
                 20                  25                  30

Arg Arg Glu Ala Glu Asp Leu Gln Val Gly G ln Val Glu Leu Gly
                 35                  40                  45

Gly Gly Pro Gly Ala Gly Ser Leu Gln Pro L eu Ala Leu Glu Gly
                 50                  55                  60

Ser Leu Gln Lys Arg Gly Ile Val Glu Gln C ys Cys Thr Ser Ile
                 65                  70                  75

Cys Ser Leu Tyr Gln Leu Glu Asn Tyr Cys A sn
                 80                  85  86
```

<210> SEQ ID NO 3
<211> LENGTH: 51
<212> TYPE: PRT
<213> ORGANISM: Homo sapiens

<400> SEQUENCE: 3

```
Phe Val Asn Gln His Leu Cys Gly Ser His L eu Val Glu Ala Leu
  1               5                  10                  15

Tyr Leu Val Cys Gly Glu Arg Gly Phe Phe T yr Thr Pro Lys Thr
                 20                  25                  30

Gly Ile Val Glu Gln Cys Cys Thr Ser Ile C ys Ser Leu Tyr Gln
                 35                  40                  45

Leu Glu Asn Tyr Cys Asn
                 50  51
```

<210> SEQ ID NO 4
<211> LENGTH: 38
<212> TYPE: DNA
<213> ORGANISM: Artificial
<220> FEATURE:
<221> NAME/KEY: Artificial
<222> LOCATION: 1-38
<223> OTHER INFORMATION: Synthesized primer

<400> SEQUENCE: 4

```
agctgctttg atatgcatct cccgaaactc tgtgcggt                              38
```

<210> SEQ ID NO 5
<211> LENGTH: 37
<212> TYPE: DNA
<213> ORGANISM: Artificial
<220> FEATURE:
<221> NAME/KEY: Artificial
<222> LOCATION: 1-37
<223> OTHER INFORMATION: Synthesized primer

<400> SEQUENCE: 5

```
gagcgatctg ggtctagaca gatttagcgg gtttcag                               37
```

<210> SEQ ID NO 6
<211> LENGTH: 24
<212> TYPE: DNA
<213> ORGANISM: Artificial
<220> FEATURE:
<221> NAME/KEY: Artificial
<222> LOCATION: 1-24
<223> OTHER INFORMATION: Synthesized oligonucleotide -continued

<400> SEQUENCE: 6
aaaagggtat gtagaggttg aggt 24

INSULIN-LIKE GROWTH FACTOR-1 PROTEIN VARIANTS

This is a non-provisional application of co-pending application(s) provisional application No. 60/170,261 filed Dec. 9, 1999, and provisional application No. 60/115,010 , filed Jan. 6, 1999, the entire disclosure of which is hereby incorporated by reference and to which applications priority is claimed under 35 USC §119.

BACKGROUND OF THE INVENTION

1. Field of Invention

This invention relates to the use of certain agonists of the insulin-like growth factors (IGFS) to treat various disorders.

2. Description of Background and Related Art

The insulin-like growth factors I and II (IGF-I and IGF-II, respectively) mediate multiple effects in vivo, including cell proliferation, cell differentiation, inhibition of cell death, and insulin-like activity (reviewed in Clark and Robinson, *Cytokine Growth Factor Rev.,* 7: 65–80 (1996); Jones and Clemmons, *Endocr. Rev.,* 16: 3–34 (1995)). Most of these mitogenic and metabolic responses are initiated by activation of the IGF-I receptor, an $\alpha_2\beta_2$-heterotetramer closely related to the insulin receptor (McInnes and Sykes, *Biopoly.,* 43: 339–366 (1997); Ullrich et al., *EMBO J.,* 5: 2503–2512 (1986)). Both proteins are members of the tyrosine kinase receptor superfamily and share common intracellular signaling cascades (Jones and Clemmons, supra). IGF-insulin hybrid receptors have been isolated, but their function is unknown. The IGF-I and insulin receptors bind their specific ligands with nanomolar affinity. IGF-I and insulin can cross-react with their respective non-cognate receptors, albeit at a 100–1000-fold lower affinity (Jones and Clemmons, supra). The crystal structure describing part of the extracellular portion of the IGF-I receptor has recently been reported (Garrett et al., *Nature,* 394: 395–399 (1998)).

Unlike insulin, the activity and half-life of IGF-I are modulated by six IGF-I binding proteins (IGFBP's 1–6), and perhaps additionally by a more distantly-related class of proteins (Jones and Clemmons, supra; Baxter et al., *Endocrinology,* 139: 4036 (1998)). IGFBP's can either inhibit or potentiate IGF activity, depending on whether they are soluble or cell-membrane associated (Bach and Rechler, *Diabetes Reviews,* 3: 38–61 (1995)). The IGFBPs bind IGF-I and IGF-II with varying affinities and specificities (Jones and Clemmons, supra; Bach and Rechler, supra). For example, IGFBP-3 binds IGF-I and IGF-II with a similar affinity, whereas IGFBP-2 and IGFBP-6 bind IGF-II with a much higher affinity than they bind IGF-I (Bach and Rechler, supra; Oh et al., *Endocrinology,* 132, 1337–1344 (1993)).

The classical IGFBP's have a molecular mass ranging from 22–31 kDa and contain a total of 16–20 cysteines in their conserved amino- and carboxy-terminal domains (Bach and Rechler, supra; Clemmons, *Cytokine Growth Factor Rev.,* 8: 45–62 (1997); Martin and Baxter, *Curr. Op. Endocrinol. Diab.,* 16–21 (1994)). The central domain connecting both cysteine-rich regions is only weakly conserved and contains the cleavage sites for IGFBP-specific proteases (Chernausek et al., *J. Biol. Chem.,* 270: 11377–11382 (1995); Clemmons, supra; Conover, *Prop. Growth Factor Res.,* 6: 301–309 (1995)). Further regulation of the IGFBP's may be achieved by phosphorylation and glycosylation (Bach and Rechler supra; Clemmons, supra). There is no high-resolution structure available for any intact member of the IGFBP family. However, the NMR structures of two N-terminal fragments from IGFBP-5 that retain IGF-binding activity have recently been reported (Kalus et al., *EMBO J.,* 17: 6558–6572 (1998)).

IGF-I is a single-chain 70-amino-acid protein with high homology to proinsulin. Unlike the other members of the insulin superfamily, the C region of the IGF's is not proteolytically removed after translation. The solution NMR structures of IGF-I (Cooke et al., *Biochemistry,* 30: 5484–5491 (1991); Hua et al., *J. Mol. Biol.,* 259: 297–313 (1996)), mini-IGF-I (an engineered variant lacking the C-chain; DeWolf et al., *Protein Science,* 5: 2193–2202 (1996)), and IGF-IL (Terasawa et al., *EMBO J.,* 13: 5590–5597 (1994); Torres et al., *J. Mol. Biol.,* 248: 385–401 (1995)) have been reported. It is generally accepted that distinct epitopes on IGF-I are used to bind receptor and binding proteins. It has been demonstrated in animal models that receptor-inactive IGF mutants are able to displace endogenous IGF-I from binding proteins and hereby generate a net IGF-I effect in vivo (Loddick et al., *Proc. Natl. Acad. Sci. USA,* 95: 1894–1898 (1998); Lowman et al., *Biochemistry,* 37: 8870–8878 (1998)). While residues Y24, Y29, Y31, and Y60 are implicated in receptor binding, IGF mutants thereof still bind to IGFBPs (Bayne et al., *J. Biol. Chem.,* 265: 15648–15652 (1990); Bayne et al., *J. Biol. Chem.,* 264: 11004–11008 (1989); Cascieri et al., *Biochemistry,* 27: 3229–3233 (1988); Lowman et al., supra.

Additionally, a variant designated (1–27,gly$^4$,38–70)-hIGF-I, wherein residues 28–37 of the C region of human IGF-I are replaced by a four-residue glycine bridge, has been discovered that binds to IGFBP's but not to IGF receptors (Bar et al., *Endocrinology,* 127: 3243–3245 (1990)).

A multitude of mutagenesis studies have addressed the characterization of the IGFBP-binding epitope on IGF-I (Bagley et al., *Biochem. J.,* 259: 665–671 (1989); Baxter et al., *J. Biol. Chem.,* 267: 60–65 (1992); Bayne et al., *J. Biol. Chem.,* 263: 6233–6239 (1988); Clemmons et al., *J. Biol. Chem.,* 265: 12210–12216 (1990); Clemmons et al., *Endocrinology,* 131: 890–895 (1992); Oh et al., supra). In summary, the N-terminal residues 3 and 4 and the helical region comprising residues 8–17 were found to be important for binding to the IGFBP's. Additionally, an epitope involving residues 49–51 in binding to IGFBP-1, -2 and -5 has been identified (Clemmons et al., *Endocrinoloy,* supra, 1992). Furthermore, a naturally occurring truncated form of IGF-I lacking the first three N-terminal amino acids (called des(1–3)-IGF-I) was demonstrated to bind IGFBP-3 with 25 times lower affinity (Heding et al., *J. Biol. Chem.,* 271: 13948–13952 (1996); U.S. Pat. Nos. 5,077,276; 5,164,370; 5,470,828).

In an attempt to characterize the binding contributions of exposed amino acid residues in the N-terminal helix, several alanine mutants of IGF-I were constructed (Jansson et al., *Biochemistry,* 36: 4108–4117 (1997)). However, the circular dichroism spectra of these mutant proteins showed structural changes compared to wild-type IGF-I, making it difficult to clearly assign IGFBP-binding contributions to the mutated side chains. A different approach was taken in a very recent study where the IGFBP-1 binding epitope on IGF-I was probed by heteronuclear NMR spectroscopy (Jansson et al., *J. Biol. Chem.,* 273: 24701–24707 (1998)). The authors additionally identified residues R36, R37 and R50 to be functionally involved in binding to IGFBP-1.

Other IGF-I variants have been disclosed. For example, in the patent literature, WO 96/33216 describes a truncated variant having residues 1–69 of authentic IGF-I. EP 742,228 discloses two-chain IGF-I superagonists which are derivatives of the naturally occurring single-chain IGF-I having an abbreviated C domain. The IGF-I analogs are of the formula: $BC^n$,A wherein B is the B domain of IGF-I or a functional analog thereof, C is the C domain of IGF-I or a functional analog thereof, n is the number of amino acids in the C domain and is from about 6 to about 12, and A is the A domain of IGF-I or a functional analog thereof.

Additionally, Cascieri et al., *Biochemistry,* 27: 3229–3233 (1988) discloses four mutants of IGF-1, three of which have reduced affinity to the Type 1 IGF receptor. These mutants are: ($Phe^{23}$,$Phe^{24}$,$Tyr^{25}$)IGF-I (which is equipotent to human IGF-I in its affinity to the Types 1 and 2 IGF and insulin receptors), ($Leu^{24}$)IGF-I and ($Ser^{24}$)IGF-I (which have a lower affinity than IGF-I to the human placental Type 1 IGF receptor, the placental insulin receptor, and the Type 1 IGF receptor of rat and mouse cells), and desoctapeptide ($Leu^{24}$)IGF-I (in which the loss of aromaticity at position 24 is combined with the deletion of the carboxyl-terminal D region of hIGF-I, which has lower affinity than ($Leu^{24}$)IGF-I for the Type 1 receptor and higher affinity for the insulin receptor). These four mutants have normal affinities for human serum binding proteins.

Bayne et al., *J. Biol. Chem.,* 264: 11004–11008 (1988) discloses three structural analogs of IGF-I: (1–62)IGF-I, which lacks the carboxyl-terminal 8-amino-acid D region of IGF-I; (1–27,$Gly^4$,38–70)IGF-I, in which residues 28–37 of the C region of IGF-I are replaced by a four-residue glycine bridge; and (1–27,$Gly^4$,38–62)IGF-I, with a C region glycine replacement and a D region deletion. Peterkofsky et al., *Endocrinology,* 128: 1769–1779 (1991) discloses data using the $Gly^4$ mutant of Bayne et al., supra, Vol. 264. U.S. Pat. No. 5,714,460 refers to using IGF-I or a compound that increases the active concentration of IGF-I to treat neural damage.

Cascieri et al., *J. Biol. Chem.* 264: 2199–2202 (1989) discloses three IGF-I analogs in which specific residues in the A region of IGF-I are replaced with the corresponding residues in the A chain of insulin. The analogs are: ($Ile^{41}$, $Glu^{45}$,$Gln^{46}$,$Thr^{49}$,$Ser^{50}$,$Ile^{51}$$Ser^{53}$,$Tyr^{55}$,$Gln^{56}$)IGF-I, an A chain mutant in which residue 41 is changed from threonine to isoleucine and residues 42–56 of the A region are replaced; ($Thr^{49}$,$Ser^{50}$,$Ile^{51}$)IGF-I; and ($Tyr^{55}$,$Gln^{56}$)IGF-I.

WO 94/04569 discloses a specific binding molecule, other than a natural IGFBP, that is capable of binding to IGF-I and can enhance the biological activity of IGF-I. WO98/45427 published Oct. 15, 1998 and Lowman et al., supra, disclose IGF-I agonists identified by phage display. Also, WO 97/39032 discloses ligand inhibitors of IGFBP's and methods for their use. Further, U.S. Pat. No. 5,891,722 discloses antibodies having binding affinity for free IGFBP-1 and devices and methods for detecting free IGFBP-1 and a rupture in a fetal membrane based on the presence of amniotic fluid in a vaginal secretion, as indicated by the presence of free IGFBP-1 in the vaginal secretion.

Despite all these efforts, the view of the IGFBP-binding epitope on IGF-I has remained diffuse and at low resolution. The previous studies most often involved insertions of homologous insulin regions into IGF-I or protein truncations (e.g. des(1–3)-IGF-I), not differentiating between effects attributed to misfolding and real binding determinants. Combining the results of all these studies is further complicated by the fact that different techniques were used to analyze complex formation of the mutant IGF forms with the IGFBP's, ranging from radiolabeled ligand binding assays to biosensor analysis.

It has been well established that the GH/IGF/IGFBP system is involved in the regulation of anabolic and metabolic homeostasis and that defects in this system may adversely affect growth, physiology, and glycemic control (Jones et al., *Endocr. Rev.,* 16: 3–34 (1995); Davidson, *Endocr. Rev.,* 8: 115–131 (1987); Moses, *Curr. Opin. Exp. Diab.,* 4: 16–25 (1997)). More recent data suggest an expanded role for IGFBPs in the regulation of both plasma levels and bioactivity of GH and IGF-I (Jones et al., supra; Lewitt et al., *Endocrinology,* 129: 2254–2256 (1991); Rosenfeld et al., "IGF-1 treatment of syndromes of growth hormone insensitivity" In: *The insulin-like growth factors and their regulatory proteins*. Eds Baxter R C, Gluckman P D, Rosenfeld R G. Excerpta Medica, Amsterdam, 1994), pp 457–463; Lee et al., *Proc. Soc. Exp. Biol. Med.,* 216: 319–357 (1997); Cox et al., *Endocrinology,* 135: 1913–1920 (1994); Lewitt et al., *Endocrinology,* 133: 1797–1802 (1993)). Alterations in IGFBP levels can lead to clinical manifestations of either IGF excess or deficiency and also contribute to GH resistance (Barreca et al., *JCEM,* 83: 3534–3541 (1998); Shmueli et al., *Hepatology,* 24: 127–133 (1996); Murphy et al., *Prog. Growth Factor Res.,* 6: 425–432 (1996); Rajkumar et al., *Endocrinology,* 136: 4029–4034 (1995); Hall et al., *Acta Endocrinol* (Copenh), 118: 321–326 (1988); Ross et al., *Clin. Endocrinol.,* 35: 47–54 (1991); Scharf et al., *J. Hepatology,* 25: 689–699 (1996)).

The two IGFBPs that appear to be most responsible for the regulation of biological activity of both IGFs and GH are IGFBP-1 and IGFBP-3. IGFBP-3 appears to be the IGFBP most responsible for regulating the total levels of IGF-I and IGF-II in plasma. IGFBP-3 is a GH-dependent protein and is reduced in cases of GH-deficiency or resistance (Jones et al., supra; Rosenfield et al., supra; Scharf et al., supra). IGFBP-1 is generally thought to be an inhibitor of IGF activity and is increased in most cases of GH-resistant states such as diabetes, renal failure, congestive heart failure, hepatic failure, poor nutrition, wasting syndromes, and most all catabolic states (Lewitt et al., 1993, supra; Barreca et al., supra; Scharf et al., supra; Bereket et al., *Endocrinology,* 137: 2238–2245 (1996); Crown and Holly, *Clin. Nutrit.,* 14: 321–328 (1995); Underwood and Backeljauw, *J. Int. Med.,* 234: 571–577 (1993); Thrailkill et al., *J. Clin. Endo. Metab.,* 82(4): 1181–1187 (1997)). Most are characterized by the following biochemical profile: deranged glucose control, inflammation, excess IGFBP-1 levels, low IGFBP-3 levels, low IGF-bioactivity, and excess GH levels (Jones et al., supra; Barreca et al., supra; Shmueli et al., supra; Murphy et al., supra; Rajkumar et al., supra; Hall et al., supra; Ross et al., supra; Bereket et al., supra; Crown and Holly, supra; Bereket et al., *Clinical Endocrinology,* 45(3):321–326 (1996); Batch et al., *J. Clin. Endo. Metab.,* 73:964–968 (1991); Powell et al., The Southwest Pediatric Nephrology Study Group, *Kidney Int.,* 51: 1970–1979(1997)).

Glucocorticoids have been associated with a decrease in protein synthesis and an increase in protein catabolism (Simmons et al., *J. Clin. Invest.,* 73: 412–420 (1984)) and with an increase in the excretion of nitrogen in urine (Sapir et al., *Clin. Sci. Mol. Med.,* 53: 215–220 (1977)). These effects may be partially mediated by a decrease in growth hormone secretion (Trainer et al., *J. Endocrinol.,* 134: 513–517 (1992)) or by direct action of glucocorticoids on the tissue level (Baron et al., *Am. J. Physiol.,* 263: E489–E492 (1992)), resulting in interference with the local production of IGF-1 and IGFBPs (McCarthy et al., *Endocrinology,* 126: 1569–1575 (1990); Lee et al., supra) and antagonism of the action of insulin (Horber et al., *Diabetes,* 40: 141–149 (1991)). Previous studies on rats have demonstrated that the catabolic action of glucocorticoid analogues, such as dexamethasone, can be counteracted by recombinant human IGF-1 and its analogues (Tomas et al., *Biochem. J.,* 282: 91–97 (1992)). In addition, insulin has been shown to ameliorate protein catabolism (Woolfson et al., *N. Eng. J. Med.,* 300: 14–17 (1979)).

Combination therapies have also been disclosed. For example, Fuller et al., *Biochem Soc Trans,* 19: 277S (1991) describes the use of insulin and IGF to stimulate cardiac protein synthesis. Umpleby et al., *Europ. J. Clin. Invest.,* 24: 337–344 (1994) discloses treatment of dogs starved overnight with insulin and IGF to determine the effects on protein metabolism. Additionally, U.S. Pat. No. 5,994,303 discloses the use of a combination of insulin and IGF-I to counteract a decrease in nitrogen balance and protein synthesis.

With respect to renal failure, IGF-I is reported to exert a variety of actions in the kidney (Hammerman and Miller, *Am. J. Physiol.* 265: F1--F14 (1993)). It has been recognized for decades that the increase in kidney size observed in patients with acromegaly is accompanied by a significant enhancement of glomerular filtration rate (O'Shea and Layish, *J. Am. Soc. Nephrol.,* 3: 157–161 (1992)). U.S. Pat. No. 5,273,961 discloses a method for prophylactic treatment of mammals at risk for acute renal failure. Infusion of the peptide in humans with normal renal function increases glomerular filtration rate and renal plasma flow (Guler et al., *Acta Endocrinol.,* 121: 101–106 (1989); Guler et al., *Proc. Natl. Acad. Sci. USA,* 86: 2868–2872 (1989); Hirschberg et al., *Kidney Int.,* 43: 387–397 (1993); U.S. Pat. No. 5,106, 832). Further, humans with moderately reduced renal function respond to short-term (four days) IGF-I administration by increasing their rates of glomerular filtration and renal plasma flow. Hence, IGF-I is a potential therapeutic agent in the setting of chronic renal failure (O'Shea et al., *Am. J. Physiol.,* 264: F917–F922 (1993)).

Use of IGF-I or its analogs to treat mammals suffering from kidney disorders such as polycystic kidney disease and related indications, renal dysplasias, and/or renal hypoplasias is described in U.S. Pat. No. 5,985,830. This patent also reports that IGF-I is an effective agent for enhancing glomerular and kidney development in mammals suffering from chronic organ injury.

Additionally, renal function can be enhanced over a period of days by the administration of IGF-I in the setting of end-stage chronic renal failure. This is important, since end-stage chronic renal failure is a condition that can only be treated with dialysis or transplantation and the incidence thereof is rapidly increasing. Diabetics and the elderly tend to have this condition. Approximately sixty percent of patients with end-stage chronic renal failure are on hemodialysis, about ten percent are on peritoneal dialysis, and the remaining about thirty percent receive a transplant. Dialysis therapy is initiated in over 50,000 patients each year in the United States. An additional 25% of patients who have reached end-stage renal failure are denied access to dialysis each year. The cost of caring for these patients on dialysis currently averages over $200 million a month. Furthermore, the patients exhibit an impaired lifestyle on dialysis. Despite the fact that IGF-I can enhance renal function for those experiencing end-stage chronic renal failure, the enhancements of the glomerular filtration rate and renal plasma flow induced by IGF-I short-term do not persist during long-term administration and incidence of side-effects is high (Miller et al., *Kidney International,* 46: 201–207 (1994)).

The dynamics of IGF-I interaction with sensitive tissues are complex and incompletely understood. Biological activity of circulating IGF-I is regulated by levels of plasma IGFBPs, which both enhance and inhibit IGF-I actions (Cohick and Clemmons, *Annu. Rev. Physiol.,* 55: 131–153 (1993); Kupfer et al., *J. Clin. Invest.,* 91: 391–396 (1993)). In addition, IGFBPs present in tissues regulate the interaction of circulating IGF-I with its receptor. Tissue IGF-I receptor density is altered by changes in levels of circulating IGF-I. In kidney, the numbers of IGF-I receptors are inversely related to levels of circulating IGF-I (Hise et al., *Clin. Sci.,* 83: 233–239 (1992)).

It is known that under some circumstances elevated levels of circulating IGF-I are associated with or directly causative of long-term changes in renal function. For example, the enhancements of insulin and PAH clearances that accompany the elevations of circulating GH and IGF-I in patients with acromegaly are sustained over years of time (Ikkos et al., *Acta Endocrinol.,* 21: 226–236 (1956)). An increase in creatinine clearance occurred within the first 12 days of IGF-I administration to a GH-insensitive Laron dwarf. The increase was progressive over the next 59 days (Walker et al., *J. Pediatr.,* 121: 641–646 (1992)).

GH stimulates the synthesis of IGFBP3 in liver (Hammerman and Miller, supra; Cohick and Clemmons, supra; Kupfer et al., supra). It is the reduction in levels of circulating GH resulting from IGF-I inhibition of pituitary GH release that is thought to result in the fall of circulating IGFBP3 in humans administered IGF-I. Because of their GH insensitivity, IGFBP3 levels are low and are increased by IGF-I in Laron dwarfs (Kanety et al., *Acta Endocrinol.,* 128: 144–149 (1993)). This difference or another in the IGF-I effector system could explain the absence of refractoriness to IGF-I in these individuals.

Walker et al., supra, found that IGF-I increased urinary calcium excretion or urinary volume. Miller et al., supra, did not see such effect. IGF-I also enhances the transport of phosphate across the proximal tubular brush border membrane (Quigley and Baum, *J. Clin. Invest.,* 88: 368–374 (1991)). Patients with long-standing acromegaly showed marked renal hypertrophy and had supranormal glomerular filtration rates, suggesting that the hyperfiltration that accompanies long-standing elevations of circulating GH and IGF-I in humans is not injurious to the kidney (Ikkos et al., supra; Hoogenberg et al., *Acta Endocrinol.,* 129: 151–157 (1993)).

Intermittent administration of IGF-I to treat chronic disorders such as chronic renal failure is disclosed in U.S. Pat. Nos. 5,565,428 and 5,741,776.

Under clinical conditions, circulating IGF-I levels are normal in pre-terminal chronic renal failure (CRF) and slightly decreased in end-stage renal disease (Powell et al., *Am. J. Kidney Dis.,* 10: 287–292 (1987); Blum et al., *Pediatr. Nephrol.,* 5: 539–544 (1991); Tönshoff et al., *J. Clin. Endocrinol. Metab.,* 80: 2684–2691 (1995); Tönshoff et al., *Pediatr. Nephrol.,* 10: 269–274 (1996)). In contrast, IGFBP-1, IGFBP-2, and low molecular weight IGFBP-3 fragments are increased in chronic renal failure serum in relation to the degree of renal dysfunction (Lee et al., *Pediatr. Res.,* 26: 308–315 (1989); Liu et al., *J. Clin. Endocrinol. Metab.,* 70: 620–628 (1990); Powell et al., *Pediatr. Res.,* 33: 136–143 (1993)). The biological action of IGF-I is mediated via the type I IGF receptor. Because IGFBPs bind IGFs with affinities similar or higher to those of the type 1 IGF receptor, the excess of unsaturated high-affinity IGFBPs in CRF serum has the ability to inhibit IGF action on target tissues by competing with the type 1 IGF receptor for IGF binding (Tönshoff et al., *Prog. Growth*

*Factor Res.,* 6: 481–491 (1995)). Indeed, increased IGFBP levels in CRF have been identified as inhibitors of IGF bioactivity both in vitro (Blum et al., supra) and in vivo (T önshoff et al., supra, 1995).

Little is known about the production rates of IGF-I and IGFBPs in CRF. It has been suggested that the constellation of increased IGFBP over normal IGFs indicates a reduced IGF-I secretion rate in CRF, because under normal conditions an increased IGF-binding capacity would be expected to be immediately saturated by IGFs produced in the liver (Blum, *Acta Paediatr. Scand.* [*Suppl*] 379: 24–31 (1991)). The previous analysis of plasma IGFBP levels in the setting of clinical CRF had also suggested that an increased IGFBP-2 production rate might contribute to elevated IGFBP levels in CRF plasma (Tönshoff et al., supra, 1995). These two hypotheses were tested by analyzing hepatic IGF-I gene expression and IGFBP-1, -2, -3, and -4 plasma levels in a rat model of experimental uremia, and by analyzing the gene expression of IGFBP-1, -2, and -4 in liver and kidney (Tönshoff et al., *Endocrinology,* 138: 938–946 (1997)). The authors found that decreased hepatic IGF-I and increased IGFBP-1 and IGFBP-2 gene expression occur in experimental uremia.

For complete reviews of the effect of IGF-I on the kidney, see, e.g., Hammerman and Miller, *Am. J. Physiol.,* 265: F1–F14 (1993) and Hammerman and Miller, *J. Am. Soc. Nephrol.,* 5: 1–11 (1994).

Treatment of patients having dysregulation of the GH/IGF axis, including renal disorders, with IGF-I may not be successful because of the abnormal distribution of IGFBPs, mainly high IGFBP-1 levels. Therefore, an IGF-I mutant with a reduced affinity for IGFBP-1 without loss of ability to bind to IGFBP-3 could be a unique and effective therapy for the clinical conditions characterized by such dysregulation.

SUMMARY OF THE INVENTION

Accordingly, in one embodiment, the invention provides an IGF-I variant wherein the amino acid residue at position 16, 25, or 49 or the amino acid residues at positions 3 and 49 of native-sequence human IGF-I are replaced with an alanine, a glycine, or a serine residue.

Also provided herein is a composition comprising the variant in a carrier, preferably a pharmaceutically acceptable carrier. Preferably, this composition is sterile.

Additionally provided herein is a method for treating a disorder characterized by dysregulation of the GH/IGF axis in a mammal comprising administering to the mammal an effective amount of the variant as described above. The mammal is preferably human and the disorder is preferably a renal disorder, more preferably renal failure.

The peptide herein can be administered alone or together with an active agent for the particular disorder being treated, for example, a renally-active agent such as BQ-123 for renal disorders.

Also contemplated herein is a kit comprising a container containing a pharmaceutical composition containing the peptide herein and instructions directing the user to utilize the composition for treating a disorder characterized by dysregulation of the GH/IGF axis in a mammal. If the disorder is a renal disorder, this kit may optionally further comprise a container containing a renally-active molecule.

For identification of the peptides herein, human IGF-I was displayed monovalently on filamentous phagemid particles (U.S. Pat. Nos. 5,750,373 and 5,821,047), and a complete alanine-scanning mutagenesis thereof (Cunningham and Wells, *Science,* 244: 1081–1085 (1989); U.S. Pat. No. 5,834,250) was performed by phage display ("turbo-ala scan") (Cunningham et al., *EMBO J.,* 13: 2508–2515 (1994); Lowman, *Methods Mol. Biol.,* 87: 249–264 (1998)). The mutant IGF-phagemids were used to map the binding determinants on IGF-I for IGFBP-1 and IGFBP-3. The alanine scanning reveals specificity determinants for these binding proteins, so as to generate binding-protein-specific IGF variants that bind specifically to IGFBP-1 or IGFBP-3 to modulate their clearance half-life, improve proteolytic stability, or alter their tissue distribution in vivo. These mutants should also be useful for mapping the functional binding site for IGF receptor, whose crystal structure was recently reported (Garrett et al., supra). In addition, it may be of interest to map the epitopes of various IGF-binding antibodies or of other peptides or proteins that bind to IGF-I.

BRIEF DESCRIPTION OF THE DRAWINGS

FIGS. 1A and 1B show a phage ELISA of the variant, G1S-A70V IGF-I, binding to IGFBP-1 (FIG. 1A) and IGFBP-3 (FIG. 1B). Microtiter plates coated with 1 $\mu$g/ml IGFBP-1 (FIG. 1A) or IGFBP-3 (FIG. 1B) were incubated with phage particles displaying G1S-A70V in the presence of the indicated amounts of soluble competitor protein, IGFBP-1 (FIG. 1A) or IGFBP-3 (FIG. 1B). The half-maximal inhibitory concentration ($IC_{50}$) of competitor, i.e., the inhibitory concentration of competitor that resulted in half-maximal binding of the phagemid in that particular experiment, is denoted for the respective IGFBP.

FIGS. 2A and 2B show the loss or gain of IGFBP affinity for the IGF-I mutants tested by phage ELISA. Relative $IC_{50}$ values ($IC_{50mut}/IC_{50G1S\text{-}A70V}$) of each IGF-I alanine mutant (affinity changes of each mutant for the binding proteins with respect to IGF-I G1S-A70V) are shown for IGFBP-1 (filled bars) and IGFBP-3 (open bars). Data are taken from Table I below. Relative $IC_{50}$ values <1 denote gain of affinity; values >1 denote loss of affinity. The asterisk indicates that these particular variants were not displayed on phage, as judged by antibody binding.

FIGS. 3A and 3B show binding specificity of the IGF-I variant F49A displayed on phage to IGFBP-1 and -3, respectively, in competitive-phage ELISA. Phagemid particles displaying F49A (squares) were bound to plates coated with IGFBP-3 in the presence of the indicated amounts of soluble IGFBP-1 (FIG. 3A) or IGFBP-3 (FIG. 3B). The same experiment was carried out in parallel with phage displaying the wild-type-like IGF-I variant G1S-A70V (circles). See Tables I and II below for absolute $IC_{50}$ values. Data points are mean±standard deviation, n=2. Immunosorbent plates were coated with 1 $\mu$g/ml IGFBP-3 and ELISA were carried out as described in the Examples below using wild-type IGF-I phage (WT, circles) and IGF-F49A phage (F49A, squares) in parallel. Experiments were carried out in duplicate, and data points are shown as mean±standard deviation.

FIG. 4 discloses a sequence alignment of native-sequence human IGF-I (designated wtIGF)(SEQ ID NO:1), native-sequence human proinsulin (designated proinsulin) (SEQ ID NO:2), and native-sequence human insulin (designated insulin (B chain) followed by insulin (A chain)) (SEQ ID NO:3). The asterisks and dots indicate sequence identity and sequence similarity, respectively, at the indicated amino acid positions among the three sequences.

FIGS. 5A–5D show a biosensor analysis of IGFBP binding to immobilized IGF-I variants. Sensorgrams are shown for IGFBP-1 (FIGS. 5A, 5C) or IGFBP-3 (FIGS. 5B, 5D) binding to immobilized wild-type IGF-I (FIGS. 5A, 5B) or F49A IGF variant (FIGS. 5C, 5D). The concentrations of ligand in each experiment were 1 $\mu$M, 500 nM, and 250 nM. See Table II for kinetic parameters.

FIGS. 6A–6B show a model of the functional binding epitopes for IGFBP-1 and IGFBP-3, respectively, on the surface of IGF-I. Amino acid side chains were classified according to their relative contribution in binding energy (Table I) and colored as follows: no effect (grey); 2–5 fold loss of apparent affinity (yellow); 5–10 fold (orange); 1 0–100 fold (bright red); >100 fold (dark red). If available, numbers from phage ELISA experiments in Table I below were used. BIACORE™ data were used instead for V11A, R36A, and P39A variants (Table II). The NMR structure of IGF-I (Cooke et al., supra) was represented using the program Insight II™ (MSI, San Diego, Calif.). The binding epitope for IGFBP-1 (FIG. 6A) is located on the "upper" and "lower" face of the N-terminal helix (residues 8–17), connected by the energetically-important residue F49. For IGFBP-3 (FIG. 6B), individual IGF-I side chains contribute very little binding energy. The binding epitope has shifted away from the N-terminus and newly includes G22, F23, Y24.

FIG. 7 shows the amount of bound IGFBP-1, determined in a competitive BIACORE™ binding experiment, plotted against the IGF variant concentration for E3A/F49A (squares) and F49A (circles).

FIGS. 8A and 8B show, respectively, the calculated IGF-I activity in nM units for several IGF-I variants at 13 nM (high) and 1.3 nM (low) variant concentrations using IGF-I KIRA optical density analysis. The signal obtained for each IGF variant was compared to that of a standard-dilution series of wild-type IGF-I, and reported in terms of an apparent IGF-I concentration corresponding to the observed activity.

FIGS. 9A and 9B show IGF receptor activation curves for F49A IGF-I (FIG. 9A) and E3A/F49A (FIG. 9B) as well as for wild-type IGF-I, as measured using serial dilutions in KIRA assays. The variants are represented by squares and the wild-type IGF-I is represented by circles.

FIGS. 10A and 10B show an assessment of preliminary pharmacological properties of F49A and E3A/F49A IGF-I, radiolabeled and administered intravenously to rats. FIG. 10A shows a time course of the rate at which both molecules are cleared from the blood of the animals, where the squares represent wild-type IGF-I, the circles represent E3A/F49A IGF-I, and the diamonds represent F49A IGF-I. FIG. 10B shows the tissue-to-blood ratio for these two IGF variants in different organs, namely, kidney, liver, spleen, heart, and pancreas, at 5, 15, and 30 minutes, where the solid bars represent wild-type IGF-I, the dotted bars represent E3A/F49A IGF-I, and the striped bars represent F49A IGF-I.

FIG. 11 shows circular dichroism spectra of wild-type IGF-I (circles), F49A IGF-I (squares), and E3A/F49A IGF-I (diamonds).

DESCRIPTION OF THE PREFERRED EMBODIMENTS

A. Definitions

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, "IGF" refers to native insulin-like growth factor-I and native insulin-like growth factor-II as well as natural variants thereof such as brain IGF, otherwise known as des(1–3)IGF-I.

As used herein, "IGF-I" refers to insulin-like growth factor-I from any species, including bovine, ovine, porcine, equine, and human, preferably human, and, if referring to exogenous administration, from any source, whether natural, synthetic, or recombinant. "Native-sequence" human IGF-I, the sequence of which is shown in FIG. 4 (SEQ ID NO:1), is prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

As used herein, "IGF-II" refers to insulin-like growth factor-II from any species, including bovine, ovine, porcine, equine, and human, preferably human, and, if referring to exogenous administration, from any source, whether natural, synthetic, or recombinant. It may be prepared by the method described in, e.g., EP 128,733.

An "IGFBP" or an "IGF binding protein" refers to a protein or polypeptide normally associated with or bound or complexed to IGF-I or IGF-II, whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA,* 92: 4472–4476 (1995) and Oh et al., *J. Biol. Chem.,* 271: 30322–30325 (1996). PSF is described in Yamauchi et al., *Biochemical Journal,* 303: 591–598 (1994). ESM-1 is described in Lassalle et al., *J. Biol. Chem.,* 271: 20458–20464 (1996). For other identified IGFBPs, see, e.g., EP 375,438 published Jun. 27, 1990; EP 369,943 published May 23, 1990; WO 89/09268 published Oct. 5, 1989; Wood et al., *Molecular Endocrinology,* 2: 1176–1185 (1988); Brinkman et al., *The EMBO J.,* 7: 2417–2423 (1988); Lee et al., *Mol. Endocrinol.,* 2: 404–411 (1988); Brewer et al., *BBRC,* 152: 1289–1297 (1988); EP294,021 published Dec. 7, 1988; Baxter et al., *BBRC,* 147: 408–415 (1987); Leung et al., *Nature,* 330: 537–543 (1987); Martin et al., *J. Biol. Chem.,* 261: 8754–8760 (1986); Baxter et al., *Comp. Biochem. Physiol.,* 91B: 229– 235 (1988); WO 89/08667 published Sep. 21, 1989; WO 89/09792 published Oct. 19, 1989; and et al., *EMBO J.,* 8: 2497–2502 (1989).

The term "body fluid" refers to a biological sample of liquid from a mammal, preferably from a human. Such fluids include aqueous fluids such as serum, plasma, lymph fluid, synovial fluid, follicular fluid, seminal fluid, amniotic fluid, milk, whole blood, urine, cerebrospinal fluid, saliva, sputum, tears, perspiration, mucus, tissue culture medium, tissue extracts, and cellular extracts.

As used herein, "human IGF receptor" refers to any receptor for an IGF found in humans and includes the Type 1 and Type 2 IGF receptors in humans to which both human IGF-I and IGF-II bind, such as the placental Type I IGF-I receptor, etc.

"Peptides" include an IGF-I agonist/IGF-I variant having at least two amino acids and include polypeptides having at least about 50 amino acids. The definition includes peptide derivatives, their salts, or optical isomers.

A "disorder characterized by dysregulation of the GH/IGF axis" refers to a condition in a mammal involving, or resulting in, defects in the GH/IGF/IGFBP system, which is involved in the regulation of anabolic and metabolic homeostasis. Such disorders are characterized by defects in growth, physiology, and/or glycemic control and those with clinical manifestations of either IGF excess or deficiency and/or GH resistance and/or deficiency, the latter being manifested by reduced levels of IGFBP-3 and/or increased levels of IGFBP-1. Examples include such disorders as hyperglycemic disorders, renal disorders, congestive heart failure, hepatic failure, poor nutrition, Turner's Syndrome, Down's Syndrome, a wasting syndrome involving a decrease in protein synthesis such as AIDS wasting, and catabolic states characterized by increased IGFBP levels (such as IGFBP-1 levels) relative to such levels in a mammal without such disorder, such as a critical illness, a disorder involving a decrease in nitrogen balance, and protein catabolism caused by glucocorticoid excess. An example of those with an excess of glucocorticoid is a patient for whom maintenance of substantially normal growth is desired such as neonates and pre-pubescent mammals exposed to high-dose steroid hormone therapy such as children with nephrotic syndrome or total villous atrophy. Further synergies are involved, for example, wherein catabolism and a renal disorder are treated because the treatment minimizes the weight loss that can frequently accompany the occurrence of renal insufficiencies or promote improved growth of the subject being treated for another disorder, of particular importance where the subject is not an adult.

Most of these disease states are characterized by the following biochemical profile: deranged glucose control, inflammation, excess IGFBP-1 levels, low IGFBP-3 levels, low IGF-bioactivity, and excess GH levels. Ascertainment of such conditions can be done through standard clinical means, for example, ELISA for levels of molecules, clinical chemistry, RIA, or bioassay (see, for example, Jones et al., supra; Davidson, supra; Moses, supra; Lewitt et al., 1991, supra; Rosenfield et al., supra; Lee et al., 1997, supra, Cox et al., supra; Lewitt et al., 1993, supra; Barreca et al., supra; Shmueli et al., supra; Murphy et al., supra; Rajkumar et al., supra; Hall et al., supra; Ross et al., supra; Scharf et al., supra; Bereket et al., *Endocrinology,* supra; Crown and Holly, supra; Underwood and Backeljauw, supra; Thrailkill et al., supra; Bereket et al., *Clinical Endocrinology,* supra; Batch et al., supra; and Powell et al., 1997, supra).

As used herein, the term "hyperglycemic disorders" refers to all forms of diabetes, such as type I and type II diabetes, as well as hyperinsulinemia and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially type I and type II diabetes. "Diabetes" itself refers to a progressive disease of carbohydrate metabolism involving inadequate production or utilization of insulin and is characterized by hyperglycemia and glycosuria.

As used herein, the term "hypoglycemic agent" refers to secretagogues, preferably oral agents, that cause the secretion of insulin by the pancreas and insulin. More preferred herein for human use are insulin and the sulfonylurea class of oral hypoglycemic agents. Examples include glyburide, glipizide, and gliclazide. In addition, agents that enhance insulin sensitivity, such as biguanides, are within this definition, and also are preferred.

As used herein, "insulin" refers to any type of insulin from any species, including bovine, ovine, porcine, equine, and preferably human, and from any source, whether natural, synthetic, or recombinant. All insulin drugs reported, for example, in Diabetes Mellitus—Theory and Practice, fourth edition, Harold Rifkin, MD, Ed. (Elsevier, N.Y., 1990), Chapter 29, and U.S. Pharmacist, 18 (Nov. Suppl.) p. 3840 (1993) are suitable herein. All the various forms of human insulin on the market are included, such as those mentioned in Jens Brange, *Galenics of Insulin. The Physico-chemical and Pharmaceutical Aspects of Insulin and Insulin Preparations* (Springer-Verlag, N.Y., 1987), page 17–40. These include Regular insulin, NPH (Neutral Protamine Hagedorn) insulin, also called Isophane Insulin, 70/30 insulin, composed of 70% NPH-insulin and 30% Regular insulin, Semilente insulin, UltraLente insulin, Lente insulin, and Humalog insulin. Preferred herein for animal use is that form of insulin from the particular species being treated, such as human insulin to treat humans.

A "renal disorder" is defined herein as renal insufficiency associated with a previous history of acute or chronic renal failure that optionally may require dialysis, including but not limited to, for example, chronic renal disorders, such as chronic renal insufficiency, end-stage chronic renal failure, primary and secondary glomerulonephritis, nephrotic syndrome, interstitial nephritis, pyelonephritis, glomerulosclerosis, e.g., Kimmelstiel-Wilson in diabetic patients, and kidney failure after kidney transplantation; as well as acute renal failure and acute tubular necrosis due to ischemia; renal dysfunction associated with diabetes or autoimmune nephropathies; adverse reactions to nephrotoxic drugs or renotoxic immunosuppressives administered for organ transplantation; acute rejection episodes in post-kidney transplantation patients; polycystic kidney disease and related indications; renal dysplasias; renal hypoplasias; congenital renal anomalies; other disorders where enhanced glomerular development is indicated such as spinal bifida, solitary kidneys, interuterine growth retardation, pediatric syndromes with growth anomalies (e.g., Turner's Syndrome and Down's Syndrome), and the like; disorders where enhanced kidney development is indicated such as those suffering from chronic organ injury, those who have undergone transplantation of a small kidney (wherein further growth of the organ is ablated), subjects suffering from renal tubule poisoning, subjects who have undergone chemotherapy (e.g., cancer patients), and the like; and physical findings such as uremia, proteinuria, and anuria. Such disorder would necessarily benefit from treatment with IGF-I, and is preferably pre-terminal or end-stage chronic renal failure or chronic renal insufficiency.

As used herein, a "renally-active molecule" is one that promotes reabsorption and retention of electrolytes or otherwise acts to treat a renal disorder. Examples are provided below.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent.

As used herein, "active" or "biologically active" IGF in the context of changing serum and tissue levels of endogenous IGF refers to IGF that binds to its receptor or otherwise causes a biological activity to occur, such as those biological activities of endogenous or exogenous IGF referred to herein.

B. Modes for Carrying Out the Invention

The invention herein relates, in one aspect, to an IGF-I variant wherein the amino acid(s) of wild-type human IGF-I at position 16, 25, or 49 or at positions 3 and 49 of native-sequence human IGF-I are replaced with an alanine, a glycine, and/or a serine residue. Preferably, one or both of the amino acids in question are replaced by an alanine or glycine residue, most preferably alanine.

The peptides of this invention can be made by chemical synthesis or by employing recombinant technology. These methods are known in the art. Chemical synthesis, especially solid phase synthesis, is preferred for short (e.g., less than 50 residues) peptides or those containing unnatural or unusual amino acids such as D-Tyr, Ornithine, amino adipic acid, and the like. Recombinant procedures are preferred for longer polypeptides. When recombinant procedures are selected, a synthetic gene may be constructed de novo or a natural gene may be mutated by, for example, cassette mutagenesis. Set forth below are exemplary general recombinant procedures.

From a purified IGF and its amino acid sequence, for example, an IGF variant that is a peptidyl mutant of an IGF parent molecule may be produced using recombinant DNA techniques. These techniques contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. Preferably, the recovered peptide is then purified to a suitable degree.

Somewhat more particularly, the DNA sequence encoding a peptidyl IGF variant is cloned and manipulated so that it may be expressed in a convenient host. DNA encoding parent polypeptides can be obtained from a genomic library, from cDNA derived from mRNA from cells expressing the peptide, or by synthetically constructing the DNA sequence (Sambrook et al., *Molecular Cloning: A Laboratory Manual (*2d ed.), Cold Spring Harbor Laboratory, N.Y., 1989).

The parent DNA is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode proteins or peptides that are capable of providing phenotypic selection in transformed cells.

For example, *E. coli* may be transformed using pBR322, a plasmid derived from an *E. coli* species (Mandel et al., *J. Mol. Biol.* 53: 154 (1970)). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-15 lambda represent expression vectors with the tac, trp, or $P_L$ promoters that are currently available (Pharmacia Biotechnology).

A preferred vector is pB0475. This vector contains origins of replication for phage and *E. coli* that allow it to be shuttled between such hosts, thereby facilitating both mutagenesis and expression (Cunningham et al., *Science,* 243: 1330–1336 (1989); U.S. Pat. No. 5,580,723). Other preferred vectors are pRIT5 and pR1T2T (Pharmacia Biotechnology). These vectors contain appropriate promoters followed by the Z domain of protein A, allowing genes inserted into the vectors to be expressed as fusion proteins.

Other preferred vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes are preferred for cloning and expressing DNA sequences to produce parent IGF-I polypeptide, segment-substituted peptides, residue-substituted peptides, and peptide variants. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis,* and other enterobacteriaceae such as *Salmonella typhimurium* or *Serratia marcesans,* and various Pseudomonas species. The preferred prokaryote is *E. coli* W3110 (ATCC 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure. *Tissue Culture,* Academic Press, Kruse and Patterson, editors (1973). Examples of such useful host cell lines are VERO and HeLa cells, Chinese Hamster Ovary (CHO) cell lines, W138, 293, BHK, COS-7 and MDCK cell lines.

A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide which can be secreted by the cell, making it possible to isolate and purify the desired peptide from the culture medium and eliminating the necessity of destroying the host cells which arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in *E. coli* as well as the subsequent purification of those gene products (Harris, in *Genetic Engineering,* Williamson, R., Ed. (Academic Press, London, Vol. 4, 1983), p. 127; Ljungquist et al., *Eur. J. Biochem.,* 186: 557–561 (1989) and Ljungquist et al., *Eur. J. Biochem.,* 186: 563–569 (1989)). Protein A fusions are often used because the binding of protein A, or more specifically the Z domain of protein A, to IgG provides an "affinity handle" for the purification of the fused protein. It has also been shown that many heterologous proteins are degraded when expressed directly in *E. coli,* but are stable when expressed as fusion proteins. Marston, *Biochem J.,* 240: 1 (1986).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein (Carter, in *Protein Purification: From Molecular Mechanisms to Large-Scale Processes,* Ladisch et al., eds. (American Chemical Society Symposium Series No. 427, 1990), Ch 13, pages 181–193).

Proteases such as Factor Xa, thrombin, and subtilisin or its mutants, and a number of others have been successfully used to cleave fusion proteins. Typically, a peptide linker that is amenable to cleavage by the protease used is inserted between the "other" protein (e.g., the Z domain of protein A) and the desired peptide. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

When peptides are not prepared using recombinant DNA technology, they are preferably prepared using solid-phase synthesis, such as that generally described by Merrifield, *J. Am. Chem. Soc.,* 85: 2149 (1963), although other equivalent chemical syntheses known in the art are employable. Solid-phase synthesis is initiated from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London), 38: 1597–1598 (1966). Chloromethylated resins are commercially available from BioRad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropyl-carbodiimide. Other appropriate coupling agents, apparent to those skilled in the art, are disclosed in E. Gross & J. Meienhofer, *The Peptides: Analysis, Structure. Biology,* Vol. I: Major Methods of Peptide Bond Formation (Academic Press, New York, 1979).

It should be recognized that the α-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis, Structure, Biology,* Vol.3: "Protection of Functional Groups in Peptide Synthesis" (Academic Press, New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl. adamantyl-oxycarbonyl, and p-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an a-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection may be by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl or 2,3,6-trimethyl-4-methoxyphenylsulfonyl, or BOC.

(4) for the hydroxyl group of Ser, Thr, or Tyr, protection may be, for example, by C1–C4 alkyl, such as t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side chain amino group of Asn or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately selected protecting group, in the case of Lys, BOC. The BOC-Lys-OH can be first coupled to the benzyhydrylamine or chloromethylated resin according to the procedure set forth in Horiki et al., *Chemistry Letters,* 165–168 (1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups are described in the literature.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexyl carbodiimide or diisopropylcarbodiimide.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem* 34: 595 (1970). The coupling reactions can be performed automatically using well known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides. Proc. Fifth Amer. Pest. Symp.,* M. Goodman and J. Meienhofer, Eds., (John Wiley, N.Y., 1977), p. 518–521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the peptides of the invention is typically achieved using conventional procedures such as preparative HPLC (including reversed phase HPLC) or other known chromatographic techniques such as gel permeation, ion exchange, partition chromatography, affinity chromatography (including monoclonal antibody columns) or countercurrent distribution.

The peptides of this invention may be stabilized by polymerization. This may be accomplished by crosslinking monomer chains with polyfunctional crosslinking agents, either directly or indirectly, through multi-functional polymers. Ordinarily, two substantially identical polypeptides are crosslinked at their C- or N-termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the alpha amino of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of the reactive side chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side chains of internal residues of the peptides or residues introduced into flanking sequences. Crosslinking through externally added crosslinking agents is suitably achieved, e.g. using any of a number of reagents familiar to those skilled in the art, for example, via carbodiimide treatment of the polypeptide. Other examples of suitable multi-functional (ordinarily bifunctional) crosslinking agents are found in the literature.

The peptides of this invention also may be conformationally stabilized by cyclization. The peptides ordinarily are cyclized by covalently bonding the—and C-terminal domains of one peptide to the corresponding domain of another peptide of this invention so as to form cyclo-oligomers containing two or more iterated peptide sequences, each internal peptide having substantially the same sequence. Further, cyclized peptides (whether cyclo-oligomers or cyclo-monomers) are crosslinked to form 1–3 cyclic structures having from 2 to 6 peptides comprised therein. The peptides preferably are not covalently bonded through α-amino and main chain carboxyl groups (head to tail), but rather are crosslinked through the side chains of residues located in the—and C-terminal domains. The linking sites thus generally will be between the side chains of the residues.

Many suitable methods per se are known for preparing mono-or poly-cyclized peptides as contemplated herein. Lys/Asp cyclization has been accomplished using Na-Boc-amino acids on solid-phase support with Fmoc/9-fluorenylmethyl (OFm) side-chain protection for Lys/Asp; the process is completed by piperidine treatment followed by cyclization.

Glu and Lys side chains also have been crosslinked in preparing cyclic or bicyclic peptides: the peptide is synthesized by solid phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Peptide Protein Res.,* 25: 171–177 (1985). See also U.S. Pat. No. 4,547,489.

Disulfide crosslinked or cyclized peptides are generated by conventional methods. The method of Pelton et al. (*J. Med. Chem.,* 29: 2370–2375 (1986)) is suitable, except that a greater proportion of cyclo-oligomers are produced by conducting the reaction in more concentrated solutions than the dilute reaction mixture described by Pelton et al., for the production of cyclo-monomers. The same chemistry is useful for synthesis of dimers or cyclo-oligomers or cyclo-monomers. Also useful are thiomethylene bridges. Lebl and Hruby, *Tetrahedron Letters,* 25: 2067–2068 (1984). See also Cody et al., *J. Med. Chem.,* 28: 583 (1985).

The desired cyclic or polymeric peptides are purified by gel filtration followed by reversed-phase high pressure liquid chromatography or other conventional procedures. The peptides are sterile filtered and formulated into conventional pharmacologically acceptable vehicles.

The starting materials required for the processes described herein are known in the literature or can be prepared using known methods and known starting materials.

If in the peptides being created carbon atoms bonded to four nonidentical substituents are asymmetric, then the peptides may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations R) or S) and both are within the scope of the present invention.

The peptides of this invention may be administered to the mammal by any suitable technique, including oral, parenteral (e.g., intramuscular, intraperitoneal, intravenous, orsubcutaneous injection or infusion, or implant), nasal, pulmonary, vaginal, rectal, sublingual, or topical routes of administration, and can be formulated in dosage forms appropriate for each route of administration. The specific route of administration will depend, e.g., on the medical history of the patient, including any perceived or anticipated side effects using the peptide, the type of peptide being administered, and the particular type of disorder to be corrected. Most preferably, the administration is by continuous infusion (using, e.g., slow-release devices or minipumps such as osmotic pumps or skin patches), or by injection (using, e.g., intravenous or subcutaneous means).

The peptide to be used in the therapy will be formulated and dosed in a fashion consistent with good medical practice, taking into account the clinical condition of the individual patient (especially the side effects of treatment with the peptide), the type of disorder, the site of delivery, the method of administration, the scheduling of administration, and other factors known to practitioners. The "effective amounts" of the peptide for purposes herein are thus determined by such considerations and must be amounts that result in bioavailability of the drugs to the mammal and the desired effect.

A preferred administration is a chronic administration of about two times per day for 4–8 weeks to reproduce the effects of IGF-I. Although injection is preferred, chronic infusion may also be employed using an infusion device for continuous subcutaneous (SC) infusions. An intravenous bag solution may also be employed. The key factor in selecting an appropriate dose for the disorder in question is the result obtained, as measured, in the case of diabetes, for example, by decreases in blood glucose so as to approximate the normal range, or by other criteria for measuring treatment of the disorder as are deemed appropriate by the medical practitioner.

As a general proposition, the total pharmaceutically effective amount of the peptide administered parenterally per dose will be in a range that can be measured by a dose-response curve. For example, IGFs bound to IGFBPs or in the blood can be measured in body fluids of the mammal to be treated to determine the dosing. Alternatively, one can administer increasing amounts of the peptide to the patient and check the serum levels of the patient for IGF-I and IGF-II. The amount of peptide to be employed can be calculated on a molar basis based on these serum levels of IGF-I and IGF-II. See Example 3 below on displacement of IGF-I tracer from IGFBPs present in human serum.

Specifically, one method for determining appropriate dosing of the peptide entails measuring IGF levels in a biological fluid such as a body or blood fluid. Measuring such levels can be done by any means, including RIA and ELISA. After measuring IGF levels, the fluid is contacted with the peptide using single or multiple doses. After this contacting step, the IGF levels are re-measured in the fluid. If the fluid IGF levels have fallen by an amount sufficient to produce the desired efficacy for which the molecule is to be administered, then the dose of the molecule can be adjusted to produce maximal efficacy. This method may be carried out in vitro or in vivo. Preferably, this method is carried out in vivo, i.e., after the fluid is extracted from a mammal and the IGF levels measured, the peptide herein is administered to the mammal using single or multiple doses (that is, the contacting step is achieved by administration to a mammal) and then the IGF levels are re-measured from fluid extracted from the mammal.

Another method for determining dosing is to use antibodies to the peptide or another detection method for the peptide in the LIFA format. This would allow detection of endogenous or exogenous IGFs bound to IGFBP and the amount of peptide bound to the IGFBP.

Another method for determining dosing would be to measure the level of "free" or active IGF in blood. For some uses the level of "free" IGF would be a suitable marker of efficacy and effective doses or dosing.

For example, one method is described for detecting endogenous or exogenous IGF bound to an IGF binding protein or the amount of the peptide herein or detecting the level of unbound IGF in a biological fluid.

This method comprises:

(a) contacting the fluid with 1) a means for detecting the peptide that is specific for the peptide (such as a first antibody specific for epitopes on the peptide) attached to a solid-phase carrier, such that in the presence of the peptide the IGF binding sites remain available on the peptide for binding to the IGF binding protein, thereby forming a complex between the means and the IGF binding protein; and 2) the peptide for a period of time sufficient to saturate all available IGF binding sites on the IGF binding protein, thereby forming a saturated complex;

(b) contacting the saturated complex with a detectably labeled second means which is specific for the IGF binding protein (such as a second antibody specific for epitopes on the IGFBP) which are available for binding when the peptide is bound to the IGF binding protein; and (c) quantitatively analyzing the amount of the labeled means bound as a measure of the IGFBP in the biological fluid, and therefore as a measure of the amount of bound peptide and IGF binding protein, bound IGF and IGF binding protein, or active IGF present in the fluid.

Given the above methods for determining dosages, in general, the amount of peptide that may be employed can be estimated, i.e., from about 10 μg/kg/day to 200 μg/kg/day might be used, based on kg of patient body weight, although, as noted above, this will be subject to a great deal of therapeutic discretion. For example, with treatment of chronic renal failure, the dose per day is preferably about 10 to 160 μg/kg, more preferably 20 to 100 μg/kg, and most preferably about 25 to 75 μg/kg.

A further method is provided to estimate the distribution of IGFs on specific IGFBPs, e.g., on IGFBP-1 or IGFBP-3 using the LIFA format.

The peptide is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers,* 22, 547–556 (1983), poly(2-hydroxyethylmethacrylate) (Langer et al., *J. Biomed. Mater. Res.,* 15: 167–277 (1981), and Langer, *Chem. Tech.,* 12: 98–105 (1982), ethylene vinyl acetate (Langer et al., supra) or poly-D-(−)-3-hydroxybutyric acid (EP 133,988). Sustained-release compositions also include a liposomally entrapped peptide. Liposomes containing the peptide are prepared by methods known per se: DE 3,218,121; Epstein et al., *Proc. Natl. Acad. Sci. U.S.A.,* 82: 3688–3692 (1985); Hwang et al., *Proc. Natl. Acad. Sci. U.S.A.,* 77: 4030–4034 (1980); EP 52,322; EP 36,676; 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

PEGylated peptides having a longer life can also be employed, based on, e.g., the conjugate technology described in WO 95/32003 published Nov. 30, 1995.

For parenteral administration, in one embodiment, the peptide is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other peptides that are known to be deleterious to polypeptides.

Generally, the formulations are prepared by contacting the peptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts, e.g., NaCl, KCl, $MgCl_2$, $CaCl_2$, etc.

The peptide typically formulated in such vehicles at a pH of from or about 4.5 to 8. It will be understood that use of certain of the foregoing excipients, carriers, or stabilizers will result in the formation of salts of the peptide. The final preparation may be a stable liquid or lyophilized solid.

Typical formulations of the peptides as pharmaceutical compositions are discussed below. About 0.5 to 500 mg of the peptide or mixture of peptides, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

The peptide to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The peptide ordinarily will be stored in unit or multi-dose containers, for example, sealed ampules or vials, as an aqueous solution or as a lyophilized formulation for reconstitution. As an example of a lyophilized formulation, 10-mL vials are filled with 5 mL of sterile-filtered 1% (w/v) aqueous solution of peptide, and the resulting mixture is lyophilized. The infusion solution is prepared by reconstituting the lyophilized peptide using bacteriostatic Water-for-Injection.

Combination therapy with the peptide herein and one or more other appropriate reagents that increase total IGF in the blood or enhance the effect of the peptide is also part of this invention. These reagents generally allow the peptide herein to release the generated IGF. For example, it is desirable to administer in conjunction with the peptide other active molecules. For example, for wasting or catabolic conditions, the peptide can be administered along with an appetite enhancer such as MEGASE™.

In addition, the peptide is appropriately administered coupled to a receptor or antibody or antibody fragment for administration.

Additional combination therapy would include a growth hormone such as human growth hormone, IGFBP-3, or IGFBP-5.

In the treatment of hyperglycemic disorders, the peptide is suitably administered along with an effective amount of a hypoglycemic agent such as a sulfonylurea or any type of insulin. The hypoglycemic agent is administered to the mammal by any suitable technique including parenterally, intranasally, orally, or by any other effective route. Most preferably, the administration is by the oral route. For example, MICRONASE™ Tablets (glyburide) marketed by Upjohn in 1.25, 2.5, and 5 mg tablet concentrations are suitable for oral administration. The usual maintenance dose for Type II diabetics, placed on this therapy, is generally in the range of from or about 1.25 to 20 mg per day, which may be given as a single dose or divided throughout the day as deemed appropriate [*Physician's Desk Reference,* 2563–2565 (1995)]. Other examples of glyburide-based tablets available for prescription include GLYNASE™ brand drug (Upjohn) and DIABETA™ brand drug (Hoechst-Roussel). GLUCOTROL™ (Pratt) is the trademark for a glipizide (1-cyclohexyl-3-[p-[2-(5-methylpyrazine carboxamide)ethyl]phenyl]sulfonyl]urea) tablet available in both 5 and 10 mg strengths and is also prescribed to Type II diabetics who require hypoglycemic therapy following dietary control or in patients who have ceased to respond to other sulfonylureas [*Physician's Desk Reference,* 1902–1903 (1995)]. Other hypoglycemic agents than sulfonylureas, such as the biguanides (e.g., metformin and phenformin) or troglitozones, or other drugs affecting insulin action may also be employed.

In the treatment of congestive heart failure, ACE inhibitors may be useful together with the peptide herein by reducing systemic vascular resistance and relieving circulatory congestion. The ACE inhibitors include but are not limited to those designated by the trademarks Accupril® (quinapril), Altace® (ramipril), Capoten® (captopril), Lotensin® (benazepril), Monopril®(fosinopril), Prinivil® (lisinopril), Vasotec® (enalapril), and Zestril® (lisinopril). One example of an ACE inhibitor is that sold under the trademark Capoten®. Generically referred to as captopril, this ACE inhibitor is designated chemically as 1-[(2S)-3-mercapto-2-methylpropionyl]-L-proline.

For renal disorders, the peptide may be suitably administered with a renally-active molecule that promotes reabsorption and retention of electrolytes such as, e.g., atrial natriuretic peptide (ANP), ANP analogs, or any variants thereof with or without receptor activity, urodilatin, human B-type natriuretic peptide (BNP), angiotensin receptor antagonist, vasopressin and its analogs, and endothelin antagonists such as antibodies or peptide antagonists. One example is BQ-123 (Ihara et al., *Life Science,* 50: 247–250 (1992); JP 51-94254A published Aug. 3, 1993; Webb et al., *Biochem. Biophys. Res. Comm.,* 185: 887–892 (1992)), a cyclic pentapeptide that is a potent and specific blocker of endothelin A receptors and blocks only the hypertrophic activity induced by endothelin-1, not CT-1, mouse LIF, or phenylephrine. Another example is the parent compound to BQ-123 described by Ihara et al., *Biochim. Biophys. Res. Comm.,* 178: 132–137 (1991). Further examples include those described in EP 647,236; EP 647,449; EP 633,259 (phenyl-sulfonyl amino-pyrimidine derivatives); EP 601, 386 sulfonamide compounds); U.S. Pat. No. 5,292,740 (phenylsulfonamidopyrimidines); and U.S. Pat. No. 5,270, 313 (phenyl-sulfonyl-aminopyrimidine derivatives). In addition, angiotensin-converting enzyme (ACE) inhibitors may be beneficial in conjunction with the IGF-I treatment of renal disorders. In addition, other means of manipulating IGF status, such as regimens of diet or exercise, are also considered to be combination treatments as part of this invention. For example, one may administer the peptide to the mammal along with a high-calorie diet or food such as ENSURE™ without or in conjunction with nutrient supplements such as ketoacid supplements.

The invention herein also contemplates using gene therapy for treating a mammal, using nucleic acid encoding the peptide. Generally, gene therapy is used to increase (or overexpress) IGF levels in the mammal. Nucleic acids which encode the peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the peptide is required. For ex vivo treatment, the patient's cells are removed, the nucleic acid is introduced into these isolated cells and the modified cells are administered to the patient either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus. The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.,* 262: 4429–4432 (1987); and Wagner et al., *Proc. Natl. Acad. Sci. USA,* 87: 3410–3414 (1990). For review of the currently known gene marking and gene therapy protocols, see Anderson et al., *Science,* 256: 808–813 (1992). See also WO 93/25673 and the references cited therein.

Kits are also contemplated for this invention. A typical kit would comprise a container, preferably a vial, for the peptide formulation comprising peptide in a pharmaceutically acceptable buffer and instructions, such as a product insert or label, directing the user to utilize the pharmaceutical formulation for treating a disorder characterized by dysregulation of the GH/IGF axis in a mammal. The kit optionally includes a container, preferably a vial, for a combination molecule, such as for renal failure a renally-active molecule.

The invention will be more fully understood by reference to the following examples. They should not, however, be construed as limiting the scope of the invention. All literature and patent citations mentioned herein are expressly incorporated by reference.

EXAMPLE 1

Alanine-Scanning Mutagenesis of IGF-I and Structural Variants

Introduction

An alanine-scanning mutagenesis approach (Cunningham and Wells, supra) was used to remove that portion of each side chain of IGF-I beyond the beta carbon. The contribution of these atoms to the free energy of binding of the peptide to IGFBP-1 or to IGFBP-3 was then assessed by competitive phage ELISA. In this assay, IGFBP-1 or IGFBP-3 is used to inhibit IGF-phage mutants from binding to an IGFBP-1- or IGFBP-3-coated immunosorbent plate. From a titration series of binding protein, binding ($IC_{50}$) can be calculated. Some mutants were also assessed for direct binding in BIACORE™ assays.

In the examples, common α-amino acids may be described by the standard one- or three-letter amino acid code when referring to intermediates and final products. By common cc-amino acids is meant those amino acids incorporated into proteins under mRNA direction. Standard abbreviations are listed in The Merck Index, 10th Edition, pp Misc-2 - Misc-3. Unless otherwise designated the common α-amino acids have the natural or "L"-configuration at the alpha carbon atom. If the code is preceded by a "D" this signifies the opposite enantiomer of the common α-amino acid. Modified or unusual α-amino acids such as norleucine (Nle) and ornithine (Orn) are designated as described in U.S. Patent and Trademark Office Official Gazette 1114 TMOG, May 15, 1990.

Based upon the results of experiments using the IGF mutant described below, it is predicted that molecules of the type claimed herein should increase active IGF levels in a subject being treated.

Materials and Methods

Construction of phagemid Vector and Mutagenesis

The gene encoding mature human IGF-I was amplified from pBKIGF2B (U.S. Pat. No. 5,342,763) using PCR primers 5'-AGC TGC TTT GAT ATG CAT CTC CCG AAA CTC TGT GCG GT-3' (SEQ ID NO:4) and 5'-GAG CGA TCT GGG TCT AGA CAG ATT TAG CGG GTT TCA GGT-3' (SEQ ID NO:5). The resulting fragment was cut with NsiI and XbaI, and ligated into pH0753 previously digested with NsiI and XbaI. pH0753 is a derivative of phGHam-g3 (Lowman et al., *Biochemistry,* 30: 10832–10838 (1991)) in which the additional XbaI site in the alkaline phosphatase promoter (PhoA) region has been deleted using the oligonucleotide 5'-AAA AGG GTA TGT AGA GGT TGA GGT-3' (SEQ ID NO:6). The ligated vector pH0753 containing the IGF-I open reading frame was named pIGF-g3. It encodes for IGF-I harboring the double mutation G1S-A70V fused to a fragment of the gene III protein (residues 249–406) from the *E. coli* bacteriophage M13. Binding of this IGF-I variant to IGFBP-1 and -3 was found to be indistinguishable from wild-type IGF-I. Alanine mutagenesis was performed using single-stranded plasmid pIGF-g3 as template (Kunkel et al., *Methods Enzymol.,* 204: 125–139 (1991)). All residues of IGF-I with the exception of cysteines and alanines were singly replaced by alanine. The resulting constructs were verified by DNA sequencing.

Binding of IGF mutants displayed on phase to IGFBP-1 and -3 (phage ELISA)

Immunosorbent plates (Nunc, MAXISORP™, 96 wells) were coated with 100 μl/well of 1 μg/mL IGFBP-1 or IGFBP-3 in PBS buffer pH 7.2 at 4° C. overnight. The plates were then blocked with 0.5% TWEEN 20™/PBS (also used as binding buffer) for 2 hours at room temperature (proteinaceous blocking agents like bovine serum albumin were avoided to prevent potential IGF or IGFBP contamination). *E. coli* cells (XL1-Blue, Stratagene) freshly transformed with phagemid vector were grown overnight in 5 mL 2YT medium (Sambrook et al., supra) in the presence of M13-VCS helper phage (Stratagene). Phage particles were harvested and resuspended in PBS buffer as described in Lowman, H. B., "Phage Display of Peptide Libraries on Protein Scaffolds," in Cabilly, S. (ed.), *Combinatorial Peptide Library Protocols* (Humana Press Inc.: Totowa, N.J., 1998), pp. 249–264. Then phage concentrations were normalized to yield a maximal ELISA signal of 0.2–0.4 for each mutant (Lowman, in Cabilly, S. (ed.), supra). Threefold serial dilutions of soluble competitor were prepared on non-absorbent microtiter plates (Nunc, F, 96 wells) with binding buffer (0.5% TWEEN™ 20/PBS) containing phage at the previously-determined concentrations. The dilution range of competitor protein extended over six orders of magnitude, starting at 5 μM for IGFBP-1 and 500 nM for IGFBP-3. After blocking, the plates containing immobilized target were washed with 0.05% TWEEN™/PBS buffer and subsequently incubated with 80 μl/well of the premixed phage-competitor solutions for 1 hour at room temperature. After washing, bound phage was detected with 80 μl/well of a solution containing a primary rabbit anti-phage polyclonal antibody and a secondary goat anti-rabbit monoclonal antibody-horseradish peroxidase conjugate in 0.5% TWEEN 20™/PBS. o-Phenylenediamine (Sigma) and tetramethylbenzidine (Kirkegaard and Perry) were used as chromogenic substrates, resulting in product detection at 492 and 450 nm, respectively. $IC_{50}$ values were determined by fitting the binding data to a generic saturation curve (Lowman, in Cabilly, S. (ed.), supra). At least two individual clones of each IGF-I mutant were assayed. Numbers in Table I represent mean±standard deviation of individually assessed $IC_{50}$ values.

Expression and Purification of IGFBP-1 and IGFBP-3

Human IGFBP-1 was expressed in CHO cells and purified from the conditioned medium as described by Mortensen et al., *Endocrinology,* 138: 2073–2080 (1997). Recombinant human IGFBP-3 has also been cloned and expressed in mammalian cells (Wood et al., *Mol. Endocrinology* 2: 1176–1185 (1988)). Purification from conditioned medium essentially followed the procedure described for IGFBP-1, with use of an IGF affinity column (Martin and Baxter, *J. Biol. Chem.,* 261: 8754–8760 (1986)).

Expression and Purification of Soluble IGF-I Mutants

Plasmid pBKIGF2B (U.S. Pat. No. 5,342,763) expresses human wild-type IGF-I fused to the leader peptide of lamB under the control of the $P_{pho}A$ promoter. For ease of site-directed mutagenesis the phage f1 origin of replication (f1 ori) was introduced into plasmid pBKIGF2B. For that purpose a 466-bp BamHI fragment containing the f1 ori was excised from pH0753 (Lowman et al., supra, 1991), while plasmid pBKIGF2B was linearized with EcoRI. Vector and fragment were both treated with Klenow enzyme to fill in restriction-site overhangs prior to blunt-end ligation. Correct constructs were selected for the ability to produce single-stranded phagemid DNA in the presence of M13VCS helper phage. The resulting phagemid vector was named pBKIGF2B-f1-ori and was used as template to construct the IGF-I ala-mutants of interest (see Table II) using the procedure of Kunkel et al., *Methods Enzymol.,*204:125–139 (1991)). Every mutagenesis step was confirmed by DNA sequencing.

Expression of IGF-I mutants was as described for the IGF-I wild-type (Joly et al.,*Proc. Natl. Acad. Sci. USA,* 95:2773–2777(1998)), but without transient overexpression of oxidoreductases. The purification procedure was based on a previous protocol (Chang and Swartz, "Single-Step Solubilization and Folding of IGF-I Aggregates from *Escherichia coli*" In Cleland, J. L. (ed.), *Protein Folding In Vivo and In Vitro* (American Chemical Society, Washington, D.C., 1993), pp.178–188), with minor adaptations. Typically, 6 g of wet cell paste (equivalent to 2 liters low phosphate medium grown for 24 hrs) was resuspended in 150 ml of 25 mM Tris-HCl pH 7.5 containing 5 mM EDTA. Cells were lysed in a microfluidizer (Microfluidics Corp., Newton, Mass.), and refractile particles containing accumulated IGF-I aggregates were collected by centrifugation at 12,000×g. Refractile particles were washed twice with lysis buffer, twice with lysis buffer containing 1% N-lauroylsarcosine (Sigma) to extract membrane proteins, and twice with lysis buffer again. Washed refractile bodies were resuspended at approximately 2 mg/ml in 50 mM CAPS (3-(cyclohexylamino)-1-propanesulfonic acid; Sigma) buffer pH 10.4 containing 2 M urea, 100 mM NaCl, 20% MeOH, and 2 mM DTT. This procedure combines solubilization of refractile bodies and subsequent oxidative refolding of IGF-I mutants (Chang and Swartz, supra). After 3 hrs at room temperature the refolding solutions were filtered through microconcentrator membranes (Centricon, Amicon) with a molecular weight cut off of 50 kDa. The majority of monomeric IGF-I was recovered in the eluate, while higher molecular weight contaminants were concentrated in the retentate. At this point IGF-I fractions were >95% pure, as judged from SDS-PAGE analysis. To separate correctly disulfide-bonded IGF-I from IGF-swap (containing two non-native disulfides; Hober et al., *Biochemistry,* 31: 1749–1756 (1992); Miller et al., *Biochemistry,* 32: 5203–5213 (1993)), refolding solutions were acidified with 5% acetic acid and loaded on a Dynamax™ C18 semi-preparative HPLC column (Varian; 10.0 mm ID) at 4 ml/min. Buffers were $H_2O$/0.1% TFA (A) and acetonitrile/0.1% TFA (B). Separation of the disulfide isomers was achieved by applying the following gradient: 0–30% B in 20 min, 30–45% B in 60 min. The ratio of native IGF-I to IGF-swap was usually about 2:1 for each mutant, with IGF-swap eluting earlier in the gradient than native IGF-I. The molecular mass of each mutant was verified by mass spectrometry. After HPLC purification, samples were lyophilized and reconstituted at approximately 1 mg/ml in 100 mM HEPES buffer, pH 7.4.

Biosensor Kinetic Measurements

The binding affinities of the IGF variants for IGFBP-1 and IGFBP-3 were determined using a BIACORE™-2000 real time kinetic interaction analysis system (Biacore, Inc., Piscataway, N.J.) to measure association ($k_a$) and dissociation ($k_d$) rates. Carboxymethylated dextran biosensor chips (CM5, BIAcore Inc.) were activated with EDC (N-ethyl-N'-(3-dimethylaminopropyl)-carbodiimide hydrochloride) and NHS (N-hydroxysuccinimide) according to the supplier's instructions. For immobilization, IGF mutants in 20 mM sodium acetate, pH 4.8, were injected onto the biosensor chip at a concentration of 50 μg/ml to yield approximately 450–600 RU's (resonance-response units) of covalently-coupled protein. Unreacted groups were blocked with an injection of 1 M ethanolamine. Kinetic measurements were carried out by injecting two-fold serial dilutions (starting at 1 μM) of either IGFBP-1 or IGFBP-3 in running buffer (PBS, 0.05% Tween 20, 0.1% ovalbumin, 0.1% sodium azide) at 25° C. using a flow rate of 20 l/min. Association rates ($k_a$) and dissociation rates ($k_d$) were calculated separately using a 1:1 Langmuir™ association model in the BIACORE™ evaluation software v. 3.0. The equilibrium dissociation constant ($K_D$) was calculated as $k_d/k_a$.

Results

Monovalent Phage Display of IGF-I

For a rapid and comprehensive alanine scan of the 70 amino acid residues of IGF-I it was first determined whether the protein could be monovalently displayed on the surface of phage M 13 (Bass et al., *Proteins,* 8: 309–314 (1990)). Phage display technology combines the advantage of rapid single-stranded DNA mutagenesis with an easy purification of the resulting mutant protein, simply by isolation of the corresponding phage particles (e.g., Cunningham et al., 1994, supra). A vector was constructed in which mature human IGF-I was fused to the carboxy-terminal domain of the M13 gene III product. This construct includes the stII signal sequence which directs the fusion protein to the periplasmic space of *E. coli* and allows monovalent display of the protein (Bass et al., supra; Lowman et al., supra, 1991). For cloning purposes the first and the last amino acids of IGF-I were changed; the resulting mutant G1S-A70V was used as the template construct for the subsequent alanine scanning mutagenesis.

When phage particles displaying IGF-I G1S-A70V were isolated and assayed in a binding competition phage ELISA for their affinity to IGFBP's, the $IC_{50}$ determined in that experiment were 8.5 nM for IGFBP-1 and 0.5 nM for IGFBP-3 (FIG. 1). These values are in good agreement with dissociation constants determined by BIACORE™ experiments using wild-type IGF-I (Heding et al., supra). Wild-type IGF-I affinities determined by radioactive immunoassays (RIA) are ~2.8 nM for IGFBP-1 and ~0.8 nM for IGFBP-3, further supporting the $IC_{50}$ values derived from phage ELISA. Additionally, phage particles displaying IGF-I G1S-A70V were efficiently captured by 11 independent monoclonal mouse anti-IGF-I antibodies immobilized on microtiter plates. These results together suggested that the displayed IGF-variant is folded correctly and accessible on the surface of the phage particles.

Ala-scanning Mutagenesis of IGF-I binding to IGFBP-1 and IGFBP-3

All residues of G1S-A70V IGF-I with the exception of the four native alanines and six cysteines were singly substituted by alanine, using the described G1S-A70V IGF-I gIII vector as a template. Additionally, the single mutants S1G and V70A and the double-mutation restoring wild-type IGF-I were constructed. Each of these constructs was expressed in *E. coli* and displayed on phage. $IC_{50}$ values for binding to IGFBP-1 and IGFBP-3 were determined by competitive phage ELISA as shown in FIG. 1. At least two different clones of every mutant were tested. The resulting $IC_{50}$ values are listed in Table I, and the loss or gain in $IC_{50}$ for each mutant with respect to GlS-A70V is graphed in FIGS. 2A and B.

TABLE I

Apparent Affinities ($IC_{50}$) of IGF-I Variants for IGFBP-1 and IGFBP-3 Determined by Phage Display[a]

| IGF-I mutant | IGFBP-1 $IC_{50}$ (nM) | IGFBP-1 relative $IC_{50}$ | IGFBP-3 $IC_{50}$ (nM) | IGFBP-3 relative $IC_{50}$ | relative specificity |
|---|---|---|---|---|---|
| S1A | 5.2 ± 0.9 | 0.6 | 0.91 ± 0.32 | 1.2 | 0.5 |
| P2A | 11.0 ± 3.7 | 1.3 | 0.81 ± 0.18 | 1.1 | 1.2 |
| E3A | 278 ± 86 | 33.9 | 1.05 ± 0.08 | 1.4 | 24.2 |
| T4A | 19.4 ± 6.4 | 2.4 | 0.80 ± 0.02 | 1.1 | 2.2 |
| L5A | 55.3 ± 11.6 | 6.7 | 1.53 ± 0.22 | 2.0 | 3.3 |
| G7A | >1000 | >100 | 4.58 ± 0.28 | 6.1 | >16 |
| E9A | 8.6 ± 0.6 | 1.0 | 1.32 ± 0.30 | 1.8 | 0.6 |
| L10A | 311 ± 87 | 37.9 | 3.55 ± 0.33 | 4.7 | 8.1 |
| V11A* | n.d. | — | n.d. | — | — |
| D12A | 4.3 ± 0.8 | 0.5 | 1.49 ± 0.38 | 2.0 | 0.3 |
| L14A | 36.7 ± 1.1 | 4.5 | 0.90 ± 0.04 | 1.2 | 3.7 |
| Q15A | 13.9 ± 0.9 | 1.7 | 1.26 ± 0.41 | 1.7 | 1.0 |
| F16A | 57.8 ± 20.1 | 7.0 | 1.32 ± 0.25 | 1.8 | 4.0 |
| V17A | 42.9 ± 3.2 | 5.2 | 3.67 ± 1.02 | 4.9 | 1.1 |
| G19A | 11.0 ± 2.3 | 1.3 | 0.90 ± 0.28 | 1.2 | 1.1 |
| D20A | 8.4 ± 4.1 | 1.0 | 1.11 ± 0.06 | 1.5 | 0.7 |
| R21A | 7.1 ± 1.6 | 0.9 | 0.58 ± 0.01 | 0.8 | 1.1 |
| G22A | 15.9 ± 2.8 | 1.9 | 2.07 ± 0.11 | 2.8 | 0.7 |

TABLE I-continued

Apparent Affinities ($IC_{50}$) of IGF-I Variants for IGFBP-1 and IGFBP-3 Determined by Phage Display[a]

| IGF-I mutant | IGFBP-1 $IC_{50}$ (nM) | IGFBP-1 relative $IC_{50}$ | IGFBP-3 $IC_{50}$ (nM) | IGFBP-3 relative $IC_{50}$ | relative specificity |
|---|---|---|---|---|---|
| F23A | 10.9 ± 1.9 | 1.3 | 2.18 ± 0.01 | 2.9 | 0.5 |
| Y24A | 13.3 ± 2.9 | 1.6 | 2.53 ± 0.76 | 3.4 | 0.5 |
| F25A | 181 ± 46 | 22.1 | 3.69 ± 0.25 | 4.9 | 4.5 |
| N26A | 9.1 ± 1.8 | 1.1 | 0.90 ± 0.07 | 1.2 | 0.9 |
| K27A | 12.8 ± 0.1 | 1.6 | 0.66 ± 0.35 | 0.9 | 1.8 |
| P28A | 9.3 ± 1.4 | 1.1 | 1.41 ± 0.05 | 1.9 | 0.6 |
| T29A | 7.3 ± 2.4 | 0.9 | 1.23 ± 0.16 | 1.6 | 0.5 |
| G30A | 7.1 ± 1.7 | 0.9 | 0.58 ± 0.11 | 0.8 | 1.1 |
| Y31A | 6.8 ± 0.5 | 0.8 | 0.73 ± 0.10 | 1.0 | 0.9 |
| G32A | 10.9 ± 1.3 | 1.3 | 0.76 ± 0.28 | 1.0 | 1.3 |
| S33A | 9.1 ± 1.0 | 1.1 | 1.01 ± 0.24 | 1.3 | 0.8 |
| S34A | 9.5 ± 0.7 | 1.2 | 1.65 ± 0.21 | 2.2 | 0.5 |
| S35A | 11.7 ± 0.6 | 1.4 | 0.47 ± 0.01 | 0.6 | 2.3 |
| R36A* | n.d. | — | n.d. | — | — |
| R37A | 12.3 ± 0.1 | 1.5 | 0.75 ± 0.08 | 1.00 | 1.5 |
| P39A* | n.d. | — | n.d. | — | — |
| Q40A | 10.2 ± 0.9 | 1.2 | 0.56 ± 0.03 | 0.7 | 1.7 |
| T41A | 13.7 ± 3.1 | 1.7 | 0.43 ± 0.06 | 0.6 | 2.9 |
| G42A | 15.7 ± 3.4 | 1.9 | 0.53 ± 0.20 | 0.7 | 2.7 |
| I43A | 31.3 ± 4.1 | 3.8 | 1.17 ± 0.07 | 1.6 | 2.4 |
| V44A | 18.8 ± 5.4 | 2.3 | 1.03 ± 0.06 | 1.4 | 1.7 |
| D45A | 4.7 ± 0.7 | 0.6 | 0.69 ± 0.21 | 0.9 | 0.6 |
| E46A | 7.9 ± 2.1 | 1.0 | 0.94 ± 0.28 | 1.3 | 0.8 |
| F49A | >1000 | >100 | 2.72 ± 1.11 | 3.6 | >28 |
| R50A | 16.2 ± 1.8 | 2.0 | 0.64 ± 0.18 | 0.9 | 2.3 |
| S51A | 13.4 ± 0.4 | 1.6 | 0.65 ± 0.35 | 0.9 | 1.9 |
| D53A | 15.3 ± 2.8 | 1.9 | 1.05 ± 0.11 | 1.2 | 1.6 |
| L54A | 23.1 ± 12.0 | 2.8 | 1.83 ± 0.91 | 2.4 | 1.2 |
| R55A | 9.0 ± 2.3 | 1.1 | 0.66 ± 0.03 | 0.9 | 1.2 |
| R56A | 13.1 ± 1.8 | 1.6 | 1.00 ± 0.19 | 1.3 | 1.2 |
| L57A | 21.8 ± 5.6 | 2.7 | 1.78 ± 0.56 | 2.4 | 1.1 |
| E58A | 11.9 ± 1.8 | 1.5 | 1.03 ± 0.47 | 1.4 | 1.1 |
| M59A | 13.1 ± 1.8 | 1.6 | 0.74 ± 0.14 | 1.0 | 1.6 |
| Y60A | 6.6 ± 1.8 | 0.8 | 0.52 ± 0.01 | 0.7 | 1.2 |
| P63A | >1000 | >100 | >100 | >100 | — |
| L64A | 12.1 ± 3.3 | 1.5 | 0.93 ± 0.03 | 1.2 | 1.2 |
| K65A | 12.4 ± 0.6 | 1.5 | 0.69 ± 0.05 | 0.9 | 1.6 |
| P66A | 9.4 ± 3.2 | 1.1 | 0.57 ± 0.12 | 0.8 | 1.5 |
| K68A | 10.5 ± 2.8 | 1.3 | 0.76 ± 0.23 | 1.0 | 1.3 |
| S69A | 12.8 ± 2.3 | 1.6 | 0.71 ± 0.62 | 1.2 | 1.3 |
| V70A | 19.1 ± 0.7 | 2.3 | 0.68 ± 0.15 | 0.9 | 2.6 |
| S1G | 11.2 ± 1.1 | 1.4 | 0.99 ± 0.42 | 1.3 | 1.0 |
| IGF-I WT | 8.4 ± 0.8 | 1.0 | 1.01 ± 0.42 | 1.3 | 0.8 |
| G1S-A70V | 8.2 ± 1.6 | 1.0 | 0.75 ± 0.32 | 1.0 | 1.0 |
| Ala(1–3)-IGF | 90.4 ± 9.6 | 11.0 | 1.12 ± 0.04 | 1.5 | 7.3 |
| Des(1–2)-IGF | 5.0 ± 0.1 | 0.6 | 0.53 ± 0.03 | 0.7 | 0.9 |

[a]The variants noted with an asterisk were not successfully displayed on phage (n.d.), as judged by antibody experiments described in the text. Relative $IC_{50}$ is defined as $IC_{50mut}/IC_{50\ G1S\text{-}A70V}$. Relative specificity is defined as relative $IC_{50\ IGFBP\text{-}1}$/relative $IC_{50\ IGFBP\text{-}3}$ for each variant.

The majority of the alanine mutants yielded only minor changes in $IC_{50}$ values in the phage ELISA. Importantly, wild-type IGF-I showed the same affinities for IGFBP-1 and IGFBP-3 as G1S-A70V in which background the alanine substitutions were performed (Table I, FIGS. 2A and B). Only a few residues caused considerable (>10-fold) losses in affinity when changed to alanine: E3, G7, L10, V11, F25, R36, P39, F49, and P63 for IGFBP-1 binding; V11, R36, P39, and P63 for IGFBP-3 binding. It has been noted that ala-substitutions of glycines and prolines can lead to structural perturbations of the protein backbone (Di Cera, *Chem. Rev.,* 98: 1563–1591 (1998)).

Only a few modest improvements in binding affinity were found by alanine replacements. S1A, D12A, and D45A showed an approximately 2-fold increase in IGFBP-I binding, while S35A and T41A showed a similar effect for IGFBP-3. However, 2-fold changes in $IC_{50}$ values are at the limit of precision in these experiments.

IGFBP-specificity Determinants

E3A, G7A, L10A, F25A, and F49 showed a differential effect in binding IGFBP-1 versus IGFBP-3. For these five IGF-I single alanine mutants the relative $IC_{50}$ for IGFBP-1 differed by more than 4-fold from the one for IGFBP-3 (FIGS. 2A and B; Table I, relative specificity). E3A and F49A showed the biggest relative specificity factors in this group. Alanine substitution of E3 had virtually no effect on IGFBP-3 affinity (1.4 fold), while binding to IGFBP-1 was weakened 34-fold. Even more dramatic, the affinity of F49A was reduced more than 100-fold for IGFBP-1 but only 3.6-fold for BP-3. This result was illustrated in a direct comparison by phage ELISA. Phage particles displaying IGF-I F49A were added to IGFBP-3 coated wells in the presence of soluble IGFBP-1 (FIG. 3A) or IGFBP-3 (FIG. 3B). Compared to control phage displaying IGF-I G1S-A70V, the binding curve of F49A shifted by more than two orders of magnitude in the IGFBP-1 competition (FIG. 3A). In contrast, the binding curves were similar in the IGFBP-3 competition, and the $IC_{50}$ values differed by less than a factor of 4 (FIG. 3B). Thus, E3 and F49 are two major specificity determinants for IGFBP-1 binding in the IGF-I molecule.

Residues G7, L10, and F25 appeared to be important for binding of both IGFBP's, although showing a more pronounced loss of affinity for IGFBP-1 than for IGFBP-3 when substituted by alanines. No significant specificity determinant for IGFBP-3 was identified, such as a mutant binding much tighter to IGFBP-1 than to IGFBP-3. However, mutations E9A, D12A, F23A, Y24A, T29A, S34A, and D45A had slightly larger (about 2-fold) effects on IGFBP-3 than on IGFBP-1 binding.

BIACORE™ Measurements of Purified Soluble IGF Mutants

For validation of the results obtained by phage ELISA, specific alanine mutants were expressed and purified for kinetic analysis using a BIACORE™ instrument. The dissociation constant ($K_D$) of wild-type IGF-I was determined to be 13 nM for IGFBP-1 and 1.5 nM for IGFBP-3 (FIGS. 5A and 5B; Table II). The difference in affinity for the IGFBP's is due to a 10-fold faster association rate ($k_a$) of IGF-I to IGFBP-3 ($3.2 \times 10^5$ versus $3.2 = 10^4$ $M^{-1}s^{-1}$). These results correspond well with the absolute $IC_{50}$ values determined by phage ELISA (FIGS. 1A and 1B; Table I). As expected, the double-mutant G1S-A70V showed kinetic parameters essentially indistinguishable from wild-type (Table II).

V11A, R36A, and P39A were tested because these variants had not been displayed correctly on phage, based upon the antibody recognition experiments (see above). R36A and P39A showed wild-type kinetics for both binding proteins, whereas V11A showed a 5-fold reduction in affinity for both IGFBP-1 and IGFBP-3.

Furthermore, it was decided to examine the soluble IGF variant T4A. This residue had been implicated in IGFBP binding in earlier publications (Bayne et al., supra, *J. Biol. Chem.* 263, Clemmons et al., supra, 1990), but had shown modest effects in the phage assays herein. The increase in the $K_D$ values of T4A relative to wild-type IGF-I was approximately 2–3-fold higher than the $IC_{50}$ ratios determined by phage ELISA (Table II). A bigger discrepancy between the results obtained by phage and the biosensor analysis was seen for F16A. In this case the two methods differed by a factor of 4.

It has been shown that mutations in the first a-helical region have a destabilizing effect on the IGF-protein structure (Jansson et al., supra, 1997). Without being limited to any one theory, it is believed that the g3 fusion protein on the surface of the phage might be more stable than the refolded, purified soluble protein. This is supported by the BIACORE™ results obtained for F25A and F49A, two residues located outside the structurally sensitive N-terminal helix. The respective changes in $K_D$ and $IC_{50}$ values are in excellent agreement for these two mutants (Table II). The differential effect of F49A on binding to the IGFBP's was confirmed by the BIACORE™ analysis. A 70-fold decrease in affinity was measured for IGFBP-1 binding (FIG. 5C; Table II), whereas IGFBP-3 binding was reduced only 4-fold (FIG. 5D; Table 11).

TABLE II

Kinetic Parameters for the Interaction of Purified IGF-I Variants with IGFBP-1 and -3 Determined by BIACORE ™ Analysis[a]
Binding to IGFBP-1

| | $k_a$ ($\times 10^4$ $M^{-1}s^{-1}$) | $k_d$ ($\times 10^4$ $s^{-1}$) | $K_D$ (nM) | relative $K_D$ | relative $IC_{50}$ |
|---|---|---|---|---|---|
| IGF-I WT | 3.2 ± 0.2 | 4.1 ± 0.2 | 13.0 ± 1.0 | 1.0 | 1.0 |
| G1S-A70V | 3.2 ± 0.2 | 4.5 ± 0.01 | 14.0 ± 0.7 | 1.1 | 1.0 |
| T4A | 1.9 ± 0.2 | 16.7 ± 1.6 | 90.0 ± 11.0 | 6.9 | 2.4 |
| V11A | 1.9 ± 0.1 | 12.3 ± 0.6 | 66.5 ± 4.5 | 5.1 | — |
| F16A | 1.9 ± 0.6 | 60.3 ± 4.5 | 321 ± 98 | 25 | 6.0 |
| F25A | 1.5 ± 0.5 | 49.0 ± 5.7 | 323 ± 107 | 25 | 22 |
| F36A | 4.0 ± 0.2 | 5.6 ± 0.2 | 13.9 ± 0.8 | 1.1 | — |
| P39A | 3.1 ± 0.2 | 4.2 ± 0.1 | 13.6 ± 0.8 | 1.0 | — |
| F49A | 1.26 ± 0.8 | 115 ± 1.5 | 913 ± 551 | 70 | >100 |
| IGF-I WT | 3.2 ± 0.5 | 4.7 ± 0.8 | 1.5 ± 0.3 | 1.0 | 1.4 |
| G1S-A70V | 2.9 ± 0.8 | 6.3 ± 0.5 | 2.2 ± 0.6 | 1.5 | 1.0 |
| T4A | 1.8 ± 0.6 | 5.5 ± 0.1 | 3.1 ± 1.0 | 2.1 | 1.1 |
| V11A | 3.1 ± 0.5 | 20.9 ± 2.8 | 6.7 ± 1.3 | 4.5 | — |
| F16A | 1.1 ± 0.4 | 11.4 ± 2.7 | 10.3 ± 4.7 | 6.9 | 1.8 |
| F25A | 1.5 ± 0.5 | 11.8 ± 0.1 | 7.7 ± 0.3 | 5.1 | 4.9 |
| R36A | 4.0 ± 0.1 | 4.7 ± 0.2 | 1.2 ± 0.2 | 0.8 | — |
| P39A | 2.7 ± 0.2 | 6.0 ± 0.3 | 2.2 ± 0.2 | 1.5 | — |
| F49A | 2.7 ± 0.7 | 17.1 ± 0.9 | 6.3 ± 1.7 | 4.2 | 3.6 |

[a]The relative changes in dissociation constants ($K_{D\ mur}/K_{D\ wt}$) are compared to the relative $IC_{50}$ values ($IC_{50\ mut}/IC_{50\ G1S\text{-}A70V}$) determined by phage display (Table I).

Role of the N-terminal IGF-I Residues

Surprisingly, the IGFBP-3 interaction was generally much less affected by the alanine substitutions than was the interaction with IGFBP-1, despite the fact that IGFBP-3 binds IGF-I with approximately 10-fold higher affinity. Apart from P63A, no alanine mutant exhibited a >6-fold reduction in IGFBP-3 affinity (FIGS. 2A and B and Table I).

It had previously been shown in biosensor experiments that des(1–3)-IGF-I binds IGFBP-3 with 25-fold reduced affinity (Heding et al., supra). This naturally-occurring form of IGF-I lacks the first three N-terminal residues and shows increased mitogenic potency, presumably due to its reduction in IGFBP-binding (Bagley et al., supra). Since none of the first three amino acid side chains seem to contribute any energy to the binding of IGFBP-3 (Table I) but nevertheless des(1–3)-IGF-I is compromised in IGFBP-3 binding, without being limited to any one theory, it is hypothesized that backbone interactions might be involved.

This hypothesis was tested by displaying on phage a triple alanine mutant (Ala(1–3)-IGF-I), substituting the first three N-terminal amino acids. If the backbone in that region contributes to the interaction with IGFBP-3 this mutant should be able to bind. Binding to IGFBP-1, however, should be reduced due to the lack of the E3 side chain (Table I). As a control the des(1–2)-IGF-I mutant was generated, testing for any potential backbone interactions with IGFBP-1 at positions 1 and 2. As expected, Ala(1–3)-IGF-I showed a decreased IGFBP-1 affinity similar to E3A but no change in IGFBP-3 affinity (Table I; FIGS. 2A and B). For des(1–2)-IGF-I, no difference in affinity was observed for both binding proteins. Combined with the observations on des(1–3)-IGF-I (Heding et al., supra), these results suggest, without limitation to any one theory, that the peptide backbone between residue 3 and 4 of IGF-I mediates important interactions with IGFBP-3.

Discussion

The functional IGFBP-1 and IGFBP-3 binding epitopes on the surface of IGF-I have been probed by alanine-scanning mutagenesis. Both binding epitopes are illustrated in FIG. 6. Individual IGF-I side-chain interactions play a much more important role for binding to IGFBP-1 than to IGFBP-3. Two major binding patches are found for IGFBP-1 (FIG. 6A). One is situated on the upper face of the N-terminal helix (composed of G7, L10, V11, L14, F25, I43, and V44) and one the lower face (composed of E3, T4, L5, F16, V17, and L54). These two binding patches are bridged by F49 and R50. For IGFBP-3, the binding epitope is more diffuse and has shifted to include G22, F23, and Y24 (FIG. 6B). Binding of IGFBP-3 is generally much less sensitive to alanine substitutions. In fact, the biggest reduction in affinity (apart from P63A, see below) is a 6-fold decrease seen for G7A. This result is intriguing since IGFBP-3 binds with 10-fold higher affinity to IGF-I than does IGFBP-1. Most probably, without limitation to any one theory, interactions originating from the IGF-I main chain backbone are contributing to the binding of IGFBP-3. This hypothesis is further substantiated by the experiments with the Ala(1–3)-IGF mutant. While the single and triple alanine substitutions have no effect on IGFBP-3 binding, deletion of the first three amino acids resulted in a 25-fold decrease in affinity (Bagley et al., supra; Clemmons et al., supra, 1992; Heding et al., supra). In summary, IGF-I uses different binding modes to associate with IGFBP-1 and IGFBP-3: a few amino acid side-chain interactions are important for binding to IGFBP-1, while backbone interactions seem to play a major energetic role for binding to IGFBP-3.

A recent publication has investigated the binding epitope on IGF-I for IGFBP-1 by heteronuclear NMR spectroscopy (Jansson et al., supra, 1998). The authors found that the IGF-I residues 29, 30, 36, 37, 40, 41, 63, 65, and 66 amongst others experienced chemical shift perturbations upon complexation with IGFBP-1 at 30° C. Furthermore, Jansson and co-workers identified R36, R37, and R50 to be part of the functional binding epitope and tested those alanine mutants in BIACORE™ experiments. The largest change in affinity observed by these authors was a 3-fold decrease for R50A. However, due to the structural flexibility of IGF-I already observed in the first NMR study of the hormone (Cooke et al., supra), Jansson et al. were unable to completely assign many residues in the NMR spectrum, including F49.

In similar studies of protein-protein interfaces it was found that only a few side-chain residues contribute to the bulk of free-binding energy (Clackson and Wells, *Science,* 267: 383–386 (1995); Kelley et al., *Biochemistry,* 34: 10383–10392 (1995)). The same holds true for the IGF-IGFBP-1 interaction. However, here, as it was noticed for tissue factor binding to factor VIIa, the magnitude of the free energy of binding ($\Delta\Delta G$) values derived from important side chains is smaller than in the case of growth hormone (Kelley et al., supra). The residues with predominant $\Delta\Delta G$ contributions were not clustered on the IGF-I surface like in the growth hormone-receptor interface (Clackson and Wells, supra), but still formed a continuous IGFBP-1 binding epitope (FIG. 6A). In contrast, the IGFBP-3 binding epitope on IGF-I was discontinuous, and side chains contributed very modest individual binding energies.

Substitution of P63 by alanine in IGF-I results in a decreased affinity for both binding proteins that cannot be measured in the concentration range used in the competition phage ELISA's. However, residue P63 is located on the opposite side of the IGF-I molecule with respect to the main binding epitope. Furthermore, it has been noticed that alanine substitutions of glycines and prolines can lead to structural changes (Di Cera, supra). In addition, Jansson et al., 1998, supra, concluded that the C-terminal part of IGF-I is not involved in direct IGFBP-1 contacts, but rather undergoes indirect conformational changes upon complex formation. An extensive characterization of antibody binding sites on IGF-I has been carried out by Mañes et al., *Endocrinology* 138: 905–915 (1997). They showed simultaneous binding of IGFBP-1 or -3 to IGF-I in complex with antibodies recognizing the C-terminal D-domain. These results further support earlier observations that the D-domain, beginning with residue P63, is not involved in binding of IGFBP-1 or -3 (Bayne et al., supra, 1988).

The major discrepancy between an $IC_{50}$ ratio obtained by phage ELISA and a BIACORE™ result was observed with residue F16. As already mentioned substitution of this residue by alanine induced structural changes in the IGF-I molecule (Jansson et al., supra, 1997). The same effect was seen with the $K_D$ in the BIACORE™ results, but the affinity decrease was less pronounced in the phage ELISA experiments (see Table II). Both BIACORE™ measurements used IGF-F16A that had been refolded during the purification procedure (Jansson et al., supra, 1997). In phage display, however, the protein of interest is translocated naturally by the secretion machinery of *E. coli.* The low protein abundance in monovalent phage display (<1 molecule per phage particle) may disfavor aggregation and misfolding. Additionally, fusing IGF-I to the truncated g3 phage protein might exert a stabilizing effect on the native structure of the peptide.

The majority of IGF-I in the circulation is found in complex with IGFBP-3 and a third protein termed acid-labile subunit (ALS) (Bach and Rechler, supra; Clemmons, *Cytokine Growth Factor Rev.,* 8:45–62 (1997); Jones and Clemmons, supra). This ternary complex of 150-kD molecular weight is unable to traverse the vasculature walls and acts as a circulating reservoir for IGF's. By this mechanism the half-life of IGF-I is dramatically increased (Simpson et al., *Growth Horm IGF Res,* 8: 83–95 (1998)). The levels of IGFBP-3 are positively regulated by IGF-I. The role of IGFBP-1, in contrast, is less clear. This class of binding proteins is generally less abundant than IGFBP-3, and its levels are negatively regulated by insulin (Bach and Rechler, supra; Clemmons, supra, 1997; Jones and Clemmons, supra).

Based on the results herein, IGFBP-specific variants of IGF-I are obtained. Combination of several alanine mutations generates a variant that binds IGFBP-1 very weakly while retaining high-affinity binding of IGFBP-3. The design of IGFBP-1 specific variants that no longer bind to IGFBP-3, can involve phage display of IGF-I and the randomization of amino acids at specific positions (Cunningham et al., 1994, supra; Lowman and Wells, *J. Mol. Biol.,* 234: 564–578 (1993)).

Conclusion

Residues in IGF-I important for binding to IGFBP-1 and IGFBP-3 have been identified. Several residues were found that determine the binding specificity for a particular IGFBP. Recent publications (Loddick et al., supra; Lowman et al., *Biochemistry,* supra, 1998)) have reported animal studies where increased pools of bioavailable "free" IGF-I were generated by displacing endogenous IGF-I from binding proteins. IGFBP-specific IGF-I variants may be used diagnostically and therapeutically as described herein.

EXAMPLE 2

Characterization of Certain Mutants Regarding Treatment of Renal Disorders

Construction of IGF-I Mutants

In Example 1 (and in Dubaquié and Lowman, *Biochemistry,* 38: 6386 (1999)) IGF-I mutants are identified in which binding affinity to IGFBP-1, IGFBP-3, or both binding proteins, was reduced. In particular, the total alanine-scanning mutagenesis of IGF-I identified glutamic acid 3 (E3) and phenylalanine 49 (F49), as well as phenylalanine 16 (F16) and phenylalanine 25 (F25) to some degree, as specificity determinants for binding to IGFBP-1. Phage display alanine-scanning results suggested that both of the side chains at positions 3 and 49 selectively contribute considerable binding energy for complex formation with IGFBP-1 (~30-fold loss in affinity for E3A, ~100 fold for F49A), while their contribution in binding energy for IGFBP-3 is not detectable (E3A) or minor (~4-fold for F49A) (see Example 1 and Dubaquié and Lowman, supra).

Further improved specificity for IGFBP-3 was likely to be attained by cumulative mutation of IGF-I, because the effects of point mutations are often additive with respect to their contribution to the free energy of binding (Wells, *Biochemistry* 29: 8509 (1990)). Therefore, a double mutant of IGF-I, E3A/F49A, was constructed by combining point mutations E3A and F49A in a single molecule. Although F16A showed a smaller IGFBP-specificity effect (Example 1 and Dubaquie and Lowman, supra), the double mutant F16A/F49A was also constructed.

Also constructed was a new point mutant of IGF-1, Y31C, containing a single putative unpaired cysteinyl thiol, to facilitate site-specific immobilization of IGF-I for binding assays. Y31C was chosen because it is outside the binding epitopes for IGFBP-1 and IGFBP-3 (Dubaquie and Lowman, supra). This immobilization technique ensures a uniform ligand population (Cunningham and Wells, *J. Mol. Biol.,* 234: 554 (1993)) for binding by the injected analyte (i.e., IGF binding protein). The advantage of this method over the previously-employed amine coupling is that the IGF-I N-terminus is unblocked and free of any potential amine linkages to the chip matrix. This may be especially important for binding analysis of IGFBP-1, which is believed to interact with side chains of the IGF-I N-terminus (Dubaquié and Lowman, supra). Y31C displayed on phage showed wild-type-like affinities for both IGFBP-1 and IGFBP-3, supporting the notion that the region around residue 31 is important in receptor binding, but forms no contact with the binding proteins (Bayne et al., *J. Biol. Chem.,* 264: 11004 (1988), supra; Bayne et al., *J. Biol. Chem.,* 265: 15648 (1989), supra).

Single-alanine variants of IGF-I, including F49A, as well as the E3A/F49A double mutant, were expressed, purified, and refolded to give the appropriate disulfide isomer as judged by HPLC analysis (Example 1 herein and Dubaquié and Lowman, supra). These variants were tested in assays of specific binding-protein binding and receptor activation.

IGFBP-1 and IGFBP-3 Binding Affinity

The binding affinities of these variants for IGFBP-1 and IGFBP-3 were compared to that of wild-type IGF-I using BIACORE™ analysis. Kinetic experiments with IGFBP-3 binding to immobilized IGF-I or variants (Table III) were carried out as described in Example 1 and in Dubaquié and Lowman, supra, and compared with F49A IGF-I and wild-type IGF-I. In this assay, the double mutant E3A/F49A was about 20-fold weaker in binding affinity to IGFBP-3 than wild-type, and the double mutant F16A/F49A was about 66-fold weaker (Table 11).

TABLE III

Kinetics of IGFBP-3 Binding to IGF-I (*data from Table II of Example 1)

| Immobilized | IGFBP-3 | | |
|---|---|---|---|
| Protein | $k_a$(× $10^5$ $M^{-1}$) | $k_d$(× $10^{-4}$ $s^{-1}$) | $K_D$(nM) |
| IGF-I* | 3.2 ± 0.5 | 4.7 ± 0.8 | 1.5 ± 0.3 |
| F49A IGF-I* | 2.7 ± 0.7 | 17.1 ± 0.9 | 6.3 ± 1.7 |
| E3A/F49A IGF-I | 0.74 ± 0.4 | 13.3 ± 0.6 | 22.2 ± 10.3 |
| F16A/F49A IGF-I | 0.4 ± 0.1 | 38.6 ± 2.7 | 99.0 ± 26.0 |

For measurements of IGFBP-1 binding to IGF-I, kinetics experiments were conducted using a single-cysteine IGF-I variant, Y31C, that was immobilized onto the sensor chip surface via a disulfide linkage (BIACORE™ System Manual Supplement, 5a-1, Pharmacia (1991)). The results are consistent (Table IV) with the binding affinity measured using wild-type IGF-I immobilized via nonspecific amine coupling to the biosensor chip (Example 1 and Dubaquié and Lowman, supra).

TABLE IV

Kinetics of IGFBP-1 Binding to IGF-I (*data from Table II of Example 1)

| | IGFBP- 1 | | |
|---|---|---|---|
| Immobilized Protein | $k_a$(× $10^4$ $M^{-1}$) | $k_d$(× $10^{-4}$ $s^{-1}$) | $K_D$(nM) |
| Y31CIGF-I | 3.9 ± 0.4 | 3.8 ± 0.1 | 10.0 ± 1.1 |
| IGF-I* | 3.2 ± 0.2 | 4.1 ± 0.2 | 13.0 ± 1.0 |

The binding of F49A and E3A/F49A to IGFBP-1 was too weak for accurate kinetic measurements. Therefore, a competitive binding assay (WO 98/45427 published Oct. 15, 1998) was performed to estimate the corresponding affinities. The single-cysteine IGF-I variant, Y31C, was used that was immobilized onto a BIACORE™ biosensor chip surface as described above. Competitive binding experiments yielding half-maximal inhibitory concentration values ($IC_{50}$) were conducted as follows: 50 nM IGFBP-1 was incubated with a dilution series of the desired IGF variant. These protein mixture solutions were injected at 5 $\mu$L/min over a B1 chip containing cysteine-coupled IGF-I Y31C (200 response units). The amount of bound IGFBP-1 was determined by subtracting non-specific binding after a 20-minute injection and plotted against the IGF variant concentration (fig. 7). The results are shown in Table V.

TABLE V

| Inhibition of IGFBP-1 Binding to Immobilized Y31C IGF-I | | |
|---|---|---|
| Immobilized Protein | Competing Protein | IGFBP-1 $IC_{50}$($\mu$M) |
| Y31C IGF-I | F49A IGF-I | 1.6 ± 0.2 |
| Y31C IGF-I | E3A/F49A IGF-I | 64 ± 9 |

Compared to wild-type IGF-I, F49A and E3A/F49A had severely decreased binding affinities for IGFBP-1. F49A bound to IGFBP-1 with an $IC_{50}$ of 1.6±0.2 $\mu$M (Table V), while preserving a high-affinity dissociation constant ($K_D$) of 6.3±1.7 nM for IGFBP-3 (Table III). Binding of E3A/F49A to IGFBP-1 was found to be even weaker, with an estimated $IC_{50}$ of 64±9 $\mu$M (Table V), while having only moderately reduced affinity ($K_D$=22.2 ±10.3 nM) for IGFBP-3 (Table III). These in vitro measurements suggest that neither IGF variant should stably associate with IGFBP-1 under physiological conditions.

KIRA Assays of IGF

Type I Receptor Activation

The Kinase Receptor Activation Assay (KIRA) specifically and quantitatively monitors the extent of cytoplasmic IGF receptor phosphorylation upon extracellular stimulation by ligand (Sadick et al., *J. Pharm. Biomed. Analysis,* 19 (6): 883–891 (1998)). Several IGF variants, G1S/A70V, T4A, V11A, F16A, F25A, F16A/F49A, R36A, P39A, and F49A, were tested in single-concentration assays of receptor activation. The IGFBP-1 and IGFBP-3 binding affinities of these variants, except for F16A/F49A, are set forth in Table II and in Dubaquie and Lowman, supra. Table VI summarizes the relative affinities and specificities from BIACORE™ measurements.

For the KIRA assay, variant concentrations were roughly estimated at 13 nM ("high concentration") or 1.3 nM ("low concentration"), based on optical density measurements. The signal obtained for each IGF variant was compared to that of a standard-dilution series of wild-type IGF-l, and reported in terms of an apparent IGF-I concentration corresponding to the observed activity in the KIRA assay (FIGS. 8A–8B). Although exact relative potencies were not measured, these results show that all tested mutants maintain the ability to activate the IGF type I receptor.

TABLE VI

Relative IGFBP-1 and IGFBP-3 Affinities of IGF-I Variants. NDB, no detectable binding; ND, not determined; *data from Table II of Example 1)

| IGF-I Variant | IGFBP-I $K_D$(mutant)/ $K_D$(IGF-I)) | IGFBP-3 $K_D$(mutant)/ $K_D$(IGF-I)) | Specificity Relative BP-1/ Relative BP-3 |
|---|---|---|---|
| G1S/A70V* | 1.1 | 1.5 | 0.7 |
| T4A* | 6.9 | 2.1 | 3.3 |
| V11A* | 5.1 | 4.5 | 1.1 |
| F16A* | 25 | 6.9 | 3.6 |
| F25A* | 25 | 5.1 | 4.9 |
| R36A* | 1.1 | 0.8 | 1.4 |
| P39A* | 1.0 | 1.5 | 0.7 |
| F49A* | 70 | 4.2 | 16.7 |
| F16A/F49A | ND | 65.6 | ND |

Table VI shows that, in addition to F49A, F16A and F25A are both substantially reduced in affinity for IGFBP-1, but less so for IGFBP-3. Both still retain biological activity based on KIRA assays (FIG. 8).

For determining relative potency of F49A and E3A/F49A, their ability to activate the type I IGF receptor was measured using serial dilutions in KIRA assays. As shown in FIGS. 9A–9B, both F49A and E3A/F49A display IGF receptor activation curves that are indistinguishable from wild-type IGF-I. The half-maximal effective concentrations ($EC_{50}$) were 20.0±1.3 ng/ml for F49A, 19.8±0.5 ng/ml for E3A/F49A, and 18.9±0.2 ng/ml and 19.8±0.6 ng/ml for wild-type IGF-I. These results strongly suggest that both IGF mutants are fully biologically active.

Blood Clearance and Renal Accumulation of IGF-I Variants in Rats

The accumulation of active IGF molecules in the kidney could potentially be beneficial in chronic or acute renal failure. These pathological conditions are characterized by abnormally high levels of IGFBP-1 and IGFBP-2, combined with a reduction of IGF-I synthesis, eventually leading to cell catabolism (Tönshoff et al., supra, 1997).

To assess preliminary pharmacological properties of F49A and E3A/F49A IGF-I, both proteins were radiolabeled and administered intravenously to rats. FIG. 10A shows a time course of the rate at which both molecules are cleared from the blood of the animals. As expected due to their decreased IGFBP affinities, both variants were cleared at a faster rate compared to wild-type human IGF-I. Interestingly, the double mutant (E3A/F49A) was cleared faster than the single mutant (F49A), correlating well with the respective affinities for the major binding protein in the serum, IGFBP-3 (Table III). FIG. 10B shows the tissue-to-blood ratio for the IGF variants in different organs. The majority of the radioactively-labeled IGF molecules were detected in the kidney, whereas radioactivity levels in the liver, spleen, heart, and pancreas were much lower. It is evident that the variants F49A and E3A/F49A accumulate at statistically significant higher levels in the kidney compared to wild-type IGF-I.

Circular Dichroism Analysis of IGF-I Variants

The circular dichroism spectra of F49A and E3A/F49A IGF-I were analyzed to test whether the introduced mutations cause major changes to the protein structure. Structural destabilization could lead to increased proteolytic susceptibility, providing an alternative explanation for the faster blood clearance rates of the IGF variants. As shown in FIG. 11, however, both mutants have virtually identical spectra to the one recorded for wild-type IGF-I. The CD spectra reveal elements of both α-helix and random coil, as expected from NMR spectroscopy of IGF-I (Cooke et al., *Biochemistry,* 30: 5484, (1991)). The thermal stability of IGF-1 could not be determined accurately by circular dichroism, presumably due to the relatively high content (~30%) of random coil (Jansson et al., *Biochemistry,* 36: 4108 (1997)) already present at room temperature. The fact that the CD spectra of both variants showed no significant deviation from wild-type IGF-I is an indication that the introduced mutations do not alter the overall structure of IGF-I.

Conclusion

From the evidence presented above, it would be expected that the single and double mutants F16A, F16G, F16S, F25A, F25G, F25S, F49A, F49G, F49S, E3A/F49A, E3A/F49G, E3A/F49S, E3S/F49A, E3G/F49S, E3G/F49S, and E3S/F49G IGF-I would be effective in treating a disorder characterized by dysregulation of the GH/IGF axis, since the alanine-substituted mutants exhibit a reduced affinity for IGFBP-1 without substantial loss of ability to bind to IGFBP-3 and are biologically active based on many tests. Further, such mutants are expected to be efficacious in treating renal disorders since F49A and E3A/F49A accumulate at statistically significant higher levels in the kidney compared to wild-type IGF-I and compared to other organs, and since the alanine-substituted mutants only weakly bind to IGFBP-1 and there is increased IGFBP-1 and IGFBP-2 gene expression in experimental uremia (Tönshoff et al., supra, 1997).

EXAMPLE 3

Treatment of Humans

This example shows the principle of how an exogenously administered peptide that binds to one or more of the IGFBPs acts to displace endogenous IGFs and how to dose a peptide herein for use in humans.

In this study human Type II diabetics were administered recombinant human IGF-I or placebo by twice daily injection at four doses (10, 20, 40 or 80 μg/kg) for 12 weeks. Blood samples were drawn, before, every two weeks during, and after (EP) the 12 weeks of treatment. The concentrations of IGF-I, IGF-II, and IGFBP-3 were measured in all the samples, with the exception of IGF-II not being measured in the samples taken from the patients treated with 10 μg/day of IGF-1.

FIG. 43 of WO 98/45427 shows the concentrations of IGF-I in the blood of the patients. The unexpected finding was the "plateau" effect of administering 40 and 80 μg of IGF-I; the same total blood concentration of IGF-I was reached with these two doses.

FIG. 44 of WO 98/45427 shows the concentrations of IGF-II in the blood of the patients. In contrast to the rising levels of IGF-I, the levels of IGF-II fell in almost a mirror image pattern to the rise in IGF-I concentrations. As with the plateauing of the rising IGF-I concentrations, the falling IGF-II concentrations also reached a plateau.

FIG. 45 of WO 98/45427 shows the concentrations of IGFBP-3 in the blood of the patients. In contrast to the clear changes in the patterns of IGF-I and IGF-II in the blood, the concentrations of IGFBP-3 showed no statistically significant or clear pattern of change.

Inspection of FIGS. 43 and 44 of WO 98/45427 reveals that the total IGF concentrations (IGF-I plus IGF-II) showed little change with treatment. This was because the rise in the concentrations of IGF-I closely matched the fall in the concentrations of IGF-II. Inspection of all three Figures shows that the dose-related changes in the concentrations of IGF-I and IGF-II in the blood of the patients were not accompanied by a reduced IGFBP-3 binding protein capacity (IGFBP-3 is the major binding protein in blood).

The obvious explanation for the fall in the concentration of IGF-II, and the plateauing of IGF-I and IGF-II concentrations, is that there is a finite amount of IGF binding protein capacity and in this experiment the doses of IGF-I used caused a dose-related displacement of IGF-II from the binding proteins.

It is a logical extension of the observations in this Example to expect that any molecule with the ability to enhance levels of active IGF would show activities similar to those shown for IGF-I in this Example. In addition, from the doses of IGF-I used and the concentrations of IGFBP and IGF-I and IGF-II demonstrated, it is simple to calculate how much of a peptide should be given to increase levels of active endogenous IGF. The molar size relative to IGF-I, the affinity of the peptide for the IGFBP, and its bioavailability would be other variables taken into account to arrive at doses that increased active IGF in a human.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

What is claimed is:

1. An insulin-like growth factor-I (IGF-I) variant wherein the amino acid residue at position 16 of native-sequence human IGF-1 is replaced with a glycine or a serine residue, or the amino acid residue at position 25 or 49 or the amino acid residues at positions 3 and 49 of native-sequence human IGF-I are replaced with an alanine, a glycine, or a serine residue.

2. The variant of claim 1 wherein the amino acid residue or residues at position 25 or 49 or at positions 3 and 49 of native-sequence human IGF-I are replaced with alanine or glycine residues.

3. The variant of claim 1 wherein the amino acid residue or residues at position 25 or 49 or at positions 3 and 49 of native-sequence human IGF-I are replaced with alanine residues.

* * * * *

UNITED STATES PATENT AND TRADEMARK OFFICE

CERTIFICATE OF CORRECTION

PATENT NO. : 6,403,764 B1 Page 1 of 1
DATED : June 11, 2002
INVENTOR(S) : Yves Dubaquie et al.

It is certified that error appears in the above-identified patent and that said Letters Patent is hereby corrected as shown below:

Title page,
Item [75], insert the following inventor's name -- Deborah L. Mortensen, Pacifica, CA --

Signed and Sealed this

Twenty-third Day of March, 2004

JON W. DUDAS
*Acting Director of the United States Patent and Trademark Office*